United States Patent
Vaughn

(10) Patent No.: US 12,370,289 B2
(45) Date of Patent: *Jul. 29, 2025

(54) DOUBLE NETWORK HYDROGEL WITH ANIONIC POLYMER AND USES THEREOF

(71) Applicant: Poly-Med, Inc., Anderson, SC (US)

(72) Inventor: Michael Aaron Vaughn, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/602,655

(22) Filed: Mar. 12, 2024

(65) Prior Publication Data

US 2024/0216583 A1   Jul. 4, 2024

Related U.S. Application Data

(63) Continuation of application No. 17/160,527, filed on Jan. 28, 2021, now Pat. No. 11,957,813, which is a continuation of application No. 15/781,265, filed as application No. PCT/US2016/064682 on Dec. 2, 2016, now Pat. No. 10,933,168.

(60) Provisional application No. 62/262,945, filed on Dec. 4, 2015.

(51) Int. Cl.
| | |
|---|---|
| *A61L 27/52* | (2006.01) |
| *C08F 222/38* | (2006.01) |
| *C08J 3/075* | (2006.01) |
| *C08J 3/24* | (2006.01) |
| *C08K 5/20* | (2006.01) |
| *C08L 33/26* | (2006.01) |

(52) U.S. Cl.
CPC .......... *A61L 27/52* (2013.01); *C08J 3/075* (2013.01); *C08J 3/246* (2013.01); *C08K 5/20* (2013.01); *C08L 33/26* (2013.01); *A61L 2430/06* (2013.01); *C08F 222/385* (2013.01); *C08J 2433/02* (2013.01); *C08L 2203/02* (2013.01)

(58) Field of Classification Search
CPC ....................................................... A61L 27/52
See application file for complete search history.

(56) References Cited

U.S. PATENT DOCUMENTS

| | | | | |
|---|---|---|---|---|
| 8,025,696 | B2 * | 9/2011 | Osada | A61L 27/26 523/113 |
| 10,933,168 | B2 * | 3/2021 | Vaughn | A61L 27/26 |
| 11,957,813 | B2 * | 4/2024 | Vaughn | A61L 27/26 |
| 2010/0029789 | A1 * | 2/2010 | Chen | A61P 43/00 514/777 |

(Continued)

OTHER PUBLICATIONS

Anirudhan, T. S.; Rejeena, S. R. J. Appl. Polym, Sci. 2014, 131, 40699 (Year: 2014).*

*Primary Examiner* — Michael F Pepitone
(74) *Attorney, Agent, or Firm* — Meunier Carlin & Curfman LLC

(57) ABSTRACT

A double network hydrogel consists of a first network and a second network, where the first network is, or includes, a first polymer that is formed, at least in part, of —$CH_2$—CH (OH)— units, and the second network is, or includes, a second polymer that is formed, at least in part, of carboxyl (COOH)-containing units or salts thereof, sulfonyl ($SO_3H$)-containing units or salts thereof, and at least one of hydroxyl (OH)-containing units or amino ($NH_2$)-containing units, where the hydrogel may be used as a cartilage replacement.

16 Claims, 21 Drawing Sheets

(56) References Cited

U.S. PATENT DOCUMENTS

2010/0210752 A1\* 8/2010 Muratoglu ............... C08J 3/075
                                                    264/28
2011/0184513 A1\* 7/2011 Myung ................ C12N 5/0621
                                                    623/5.16

\* cited by examiner

| Sample Name | PVA, wt. %/mol% | Chemical X-linked Hydrogel, wt. %/mol% | AA, wt. %/mol% | AMPS, wt. %/mol% | AAm, wt. %/mol% | TRIS AAm, wt. % | MBAA, wt. %/mol% |
|---|---|---|---|---|---|---|---|
| DN-1 | 70/85 | 30/15 | 45/65 | 45/20 | 10/15 | 0 | 1/0.5 |
| DN-2 | 70/85 | 30/15 | 45/65 | 45/20 | 10/15 | 0 | 2/1.25 |
| DN-3 | 80/90 | 20/10 | 45/60 | 45/25 | 10/15 | 0 | 2/1.25 |
| DN-4 | 90/95 | 10/5 | 45/65 | 45/20 | 10/15 | 0 | 2/1.25 |
| DN-5 | 80/90 | 20/10 | 45/65 | 45/20 | 10/15 | 0 | 0.5/0.25 |
| DN-6 | 80/90 | 20/15 | 10/10 | 10/5 | 80/85 | 0 | 0.5/0.25 |
| DN-7 | 80/90 | 20/10 | 10/20 | 80/60 | 10/20 | 0 | 0.5/0.5 |
| DN-8 | 60/85 | 40/15 | 5/10 | 10/10 | 0 | 85/80 | 0.5/0.5 |
| DN-9 | 75/85 | 25/15 | 10/10 | 25/10 | 65/80 | 0 | 1.0/0.5 |

Polyvinyl Alcohol—PVA; Anionic Monomers—Acrylic Acid (AA), 2-Acrylamido-2-methylpropane sulfonic acid (AMPS) Non-Ionic Monomer—Acrylamide (AAM) TRIS acrylamide (TRIS AAm); Crosslinker—N,N,—methylenebisacrylamide; Based on 20% PVA solution

*FIG. 7*

| Sample Name | Young's Modulus (MPa) | Water Volume Fraction, % |
|---|---|---|
| 15 % PVA | 0.175±0.019 | 85.5±0.9 |
| 20 % PVA | 0.384±0.013 | -- |
| DN-1 | 0.493±0.018 | 87.9±0.1 |
| DN-2 | 0.485±0.052 | 87.8±0.1 |
| DN-3 | 0.480±0.016 | 87.1±0.1 |
| DN-4 | 0.518±0.056 | 83.5±0.4 |
| DN-5 | 0.512±0.024 | 87.0±0.1 |

FIG. 8

| Sample Name | Concentration (wt. %) | Freezing Temperature (°C) / Freezing Rate (°C/min) | Young's Modulus (MPa) | Poisson's Ratio | Shear Modulus (MPa) |
| --- | --- | --- | --- | --- | --- |
| C30-20 | 30% | -20/ -0.08 (bottom) -0.04 (middle) | 0.873±0.028 | 0.404±0.014 | 0.311±0.011 |
| C30-80 | 30% | -80/ -9.81 (bottom) -2.78 (middle) | 0.742±0.002 | 0.382±0.036 | 0.271±0.003 |
| C15-80 | 15% | -80/ -2.80 (bottom) -0.23 (middle) | 0.175±0.019 | 0.545±0.008 | 0.057±0.006 |

FIG. 13

| Sample Name | Percent Crystallinity (%) | Water Volume Fraction (%) |
|---|---|---|
| P30-80 | 54.7 ± 3.6 | 76.29 ± 0.11 |
| P30-20 | 59.6 ± 6.2 | 75.76 ± 0.14 |
| P15-80 | 58.1 ± 3.8 | 85.54 ± 0.85 |

FIG. 14

| Sample Name | Median and Range of Cell Viability Scoring |
|---|---|
| 20% PVA | 0(0,1) |
| DNH3 | 0(0,0) |
| DNH4 | 1(1,3) |
| UHMWPE | 0(0,3) |
| Media | 0(0,1) |
| Rubber | 4(4,4) | ns and 51,345 hip replacement
DOUBLE NETWORK HYDROGEL WITH ANIONIC POLYMER AND USES THEREOF

CROSS-REFERENCE TO RELATED APPLICATION

This application is a continuation of U.S. patent application Ser. No. 17/160,527, filed Jan. 28, 2021, and issued on Apr. 16, 2024, as U.S. Pat. No. 11,957,813, which is a continuation of U.S. patent application Ser. No. 15/781,265, filed Jun. 4, 2018, and issued on Mar. 2, 2021, as U.S. Pat. No. 10,933,168, which is a United States National Phase Application of International Patent Application No. PCT/US16/64682, filed Dec. 2, 2016, which claims the benefit under 35 U.S.C. § 119 (e) of U.S. Provisional Patent Application No. 62/262,945 filed Dec. 4, 2015, each of which is incorporated herein by reference in its entirety for all purposes.

FIELD OF THE INVENTION

The present invention relates to a material for double network hydrogels that mimics soft tissue properties.

BACKGROUND

Between 2007 and 2009, fifty million U.S. adults were diagnosed with having a form of arthritis, and an estimated 67 million adults are expected to be living with some arthritis-attributable activity limitation by 2030. Arthritis is commonly characterized by acute or chronic inflamed joints resulting in pain and stiffness. Specifically, the most common type of arthritis is osteoarthritis (OA), which affects joints by causing degeneration of cartilage and subchondral bone. The Center for Disease Control and Prevention (CDC) reported that in 2010 an estimated 27 million Americans are living with OA. From this, treatment for OA patients costs a total of $185 billion a year.

The risk factors associated with osteoarthritis are obesity, sex, older age, joint injury, genetics, occupation, bone deformities, lack of exercise, and other diseases. Of these risk factors, aging is the primary risk for osteoarthritis. A specific example of this is illustrated by nearly one out of two adults (age 85) will have symptomatic knee OA and two out of three that are obese. Symptomatic patients with joint pain typically follow a stepped model of care to reduce pain. First, obese patient receive recommendations to lose weight. In addition, patients are advised to increase physical activity and stretch to reduce stiffness. After this, patients are typically recommended to take nonsteroidal anti-inflammatory drugs (NSAIDs) or potentially supplement with glucosamine and chondroitin. If pain persists, a physician may suggest an intra-articular steroid or intra-articular hyaluronic acid injection. The last alternative is usually a surgical intervention.

One of the most common types of surgical intervention for patients with OA is total knee (TKR) and total hip (THR) replacement. In 2010, a total of 719,000 knee replacements and 332,000 hip replacements were performed in the US. However, other arthroplasty procedures are used to repair diseased shoulders, elbows, ankles, toes, fingers, and intervertebral discs. Orthopedic devices for arthroplasty have demonstrated success in improving the quality of life of millions per year. However, failures persist in these arthroplasty procedures, and when they occur, the impact on the patient is significant, usually requiring a second revision surgery. Between Oct. 1, 2005 and Dec. 31, 2006, 60,355 knee replacement revisions and 51,345 hip replacement revisions, which had an average cost of $49,360 and $54,553 per patient. In addition, revision surgery for TKR is typically linked with a higher complication rate, larger loss of blood, longer hospital stays, and increased operating room time when compared to primary TKR.

Typically, the failure of knee arthroplasty is divided into two separate subgroups of early and late failures as they occur due to different mechanism. In early failures (<2 years), the primary reason for failure is deep infection and instability, which is thought to be a result of the surgical procedure. However, the long term (>2 years) failure of knee replacements occur due to aseptic loosening and polyethylene wear. Patients exhibiting joint pain in their 40s to 50s are left balancing the risk of having arthroplasty at a younger age to reduce pain with the possibility of a revision surgery later in life. It is clear that many patients are accepting this risk and having arthroplasty at a younger age as approximately 50% of all TKR and THR were performed on patients 45-65 years old in 20107. As many patients don't like the risk of a potential revision arthroplasty later in life, many are living with joint pain and delaying arthroplasty. However, delaying TKR has shown indications of worse outcomes.

Therapy aimed at reducing cartilage loss may delay knee replacement. In order to address this problem, more alternative therapies for older patients with cartilage lesions and osteoarthritis are needed. One such approach has been to design synthetic cartilage materials to replace local defects and damaged tissue. PVA hydrogels have already shown promise at reducing pain and allowing patients to continue an active life style for years after implantation in knee chondral defects. However, challenges still exist in creating soft tissue materials that can both mimic the biphasic mechanical and tribological response of native cartilage and can be attached to the surrounding subchondral bone.

Cartilage is commonly described as a flexible connective tissue which is primarily characterized in three basic categories of elastic cartilage, fibrocartilage, and hyaline cartilage. Articular cartilage is a form of hyaline cartilage that is a thin connective tissue covering diarthrodial joints. Between joints, cartilage provides a surface for bone that is shock absorbing, low-friction, and wear resistant. The ability of articular cartilage to maintain this functionality is paramount for proper joint motion and health. The basic science and mechanics of fibrocartilage cartilage tissue such as the meniscus and intervertebral disc has been previously described Articular cartilage may be viewed as a three phase system consisting of a solid, fluid, and ion phase. The fluid phase is the largest component of cartilage with 60-80% of the wet weight of cartilage being water. The solid phase is composed of collagen, chondrocytes, proteoglycans, and glycoproteins. Of the solid phase, collagen is the primary component consisting of 50-80% of the dry weight. In terms of wet weight, type II collagen is 15-22% of the articular cartilage composition, and proteoglycans account for 4-7%. The ion phase is represented by electrolytes that are solubilized in the fluid phase. The electrolytes exist as both anions and cations with some common ionic species of Na+, K+, and Cl−.

The unique mechanical characteristic of articular cartilage is derived from the extracellular matrix (ECM). The structure and composition of the ECM is critical to providing much of the compressive strength, tensile strength, shear strength, low friction, and wear characteristics of cartilage. Many types of collagen such as type II, III, VI, IX, X, XI, XII and XIV exist in mature articular cartilage. However, the primary component in articular cartilage is type II collagen. Collagen II fibrils provide both tensile and shear strength depending on the orientation and depth in articular cartilage. Additionally, cartilage tensile strength and stiffness have been correlated to increase with pyridinoline cross-links of type IX collagen. The collagen fibrils in cartilage also indirectly affect the compressive strength through limiting the swelling and hydration from proteoglycans.

The majority of proteoglycans are organized into large aggregates of brush like structures. In these structures, hyaluronic acid is the backbone with aggrecan attached through a linker protein. The brush-like structures are formed through glycosaminoglycans (GAG), such as chondroitin sulfate and keratin sulfate, branching off of the large aggrecan proteoglycan. In cartilage, this unique structure of proteoglycan aggregates allows for entanglement within the collagen structure. For this structure, the GAG content produces a high density of negative charges through carboxyl ($COO^-$) and sulfate ($SO_4^-$) moieties. The physical quantity of these negative charges is typically referred to as the fixed charge density (FCD) in cartilage with properties ranging from 0.04 to 0.2 mEq/mL. Proteoglycans affect the mechanical properties of the cartilage tissue by generating osmotic pressure known as the Donnan osmotic pressure. Nearly half of the equilibrium stiffness of cartilage has been attributed to the fluid pressurization caused through the Donnan osmotic pressure. Thus loss in PG content, as exhibited in OA, can result in disruption in normal cartilage function through decrease in the aggregate modulus, increase in water content, and decrease in the coefficient of friction.

Articular cartilage has four distinct zones where the composition, morphology, and mechanical properties of the ECM differ between the articulating surface and subchondral bone. The four zones are typically characterized as the superficial zone, middle zone, deep zone, and calcified zone. The superficial zone serves as the articulating surface that is furthest away from the subchondral bone. The extracellular matrix in the superficial zone consists of the highest density of collagen in articular cartilage. In addition, the morphology of the collagen in the superficial zone is unique consisting of fine collagen fibrils which are aligned parallel to the articulating surface. While the collagen content is the highest, the proteoglycan density is the lowest in the superficial zone. This ECM matrix composition in the superficial zone allows for distinct mechanical properties that lend to high tensile strength, shear strength, and fluid permeability but a reduced aggregate modulus and fixed charge density as a result of lower proteoglycan concentration.

The middle (transitional) zone consists of 40-60% by weight of articular cartilage. In this transitional zone, the ECM has increased proteoglycan content in relation to the superficial zone. The collagen fibers in the middle zone have a larger diameter and are randomly arranged with a partial alignment at 45° as the collagen fiber alignment transitions from parallel in the superficial zone to perpendicular in the deep zone. The differences in ECM between the superficial and the middles zone result in a decrease in tensile modulus and increase in compressive modulus and fixed charged density.

Collagen fibers in the deep zone extend radially from the tidemark, a division between calcified and non-calcified cartilage. Here, the type II collagen fibers have the largest diameter serving to anchor the soft tissue to the sub-chondral bone. In addition, the proteoglycan content is highest in the deep zone. The mechanical properties of articular cartilage in the deep zone have a high aggregate modulus and shear modulus but a lower tensile modulus.

In designing biomaterials for articulating joints, the mechanical mechanism of cartilage tissue must be understood in order to mimic the functional loading of this tissue. One factor to consider is the compressive loading mechanism of articular cartilage under creep and stress relaxation through a biphasic theory. The biphasic theory defines cartilage as an elastic solid phase and a viscous fluid phase similar to a linear poroelastic model. The internal forces on cartilage upon loading are described by the stresses on the solid matrix (collagen and proteoglycan), the fluid pressurization within the porous solid phase, and the frictional drag forces between both of the fluid and solid phases. Therefore, as cartilage is compressed, a volume change occurs with stresses on the solid matrix. With the volume change, fluid pressurization inside the tissue begins which results in fluid flow out of the tissue. The fluid flowing out of the tissue is capable of high frictional drag force as the fluid flows through the small diameter porous network. In this theory, much of the compressive strength of articular cartilage arises from the low hydraulic permeability ($10^{-15}$ $m^4/N*s$) of the tissue. As a result of fluid flow from the cartilage tissue, the overall volume change of the cartilage tissue is minimal.

Additional theories such as the biphasic poroviscoelastic model, triphasic model, and the transversely isotropic biphasic model have expanded on the biphasic theory. The triphasic theory specifically incorporates the fixed charge density from the glycosaminoglycans by the Donnan osmotic pressure. In contrast to the biphasic theory, the equilibrium stiffness in the triphasic theory is now a result of not only the solid matrix but a function of the Donnan osmotic pressure. In a biphasic poroviscolelastic model, the solid phase is modeled to have an intrinsic viscoelasticity. This model differed from the biphasic model as energy dissipation could now occur through both the frictional interstitial fluid flow and intrinsic viscoelasticity of the solid matrix. The transversely isotropic biphasic model modified the bulk isotropic conditions in the biphasic model to assume isotropic conditions in the transverse plane. This model now included intrinsic mechanical properties of the hydraulic permeability, elastic modulus, and Poisson's ratio in both the axial and transverse plane. The transversely isotropic biphasic model is useful in both modeling the loading response of growth plate tissue and in tissue such as the meniscus that has aligned collagen fibers in one direction. Due to the increasing complexity of each of these cartilage mechanical models, the biphasic model is most often used to describe cartilage mechanics.

Experimental evaluation of the biphasic theory is normally conducted under unconfined compression, confined compression, and indentation testing. In modeling using the biphasic theory, the only material properties needed are the Young's modulus, Poisson's ratio and hydraulic permeability. The Young's modulus can be measured through the stress strain response of an unconfined compression test, and the Poison's ratio may be determined by measuring the equilibrium lateral expansion through optical techniques. Typically, the hydraulic permeability is determined from curve fitting the stress relaxation or creep response of the material under compression. With Young's modulus and Poisson's ratio, other intrinsic, equilibrium elastic constants may be determined such as the aggregate modulus. However, the aggregate modulus may be determined directly though confined compression test.

The tribology of cartilage implies studying the application of friction, lubrication and wear. Of these, the wear of cartilage is of primary concern as cartilage is an avascular tissue with limited capability of tissue regeneration. However, no direct theories exist to describe and predict the wear of cartilage in vivo. The complexities of this arise because cartilage tissue exhibits wear under mechanical, chemical, and mechano-chemical stimuli. The biochemical cues that result in cartilage degradation such as proteolytic enzymes have been investigated. Cartilage tribology has progressed through empirical studies that evaluate the wear and coefficient of friction under an array of conditions such as sliding speed, stroke length, pin/disc material, lubricant, loading conditions, and normal force.

The coefficient of friction for cartilage in the hip has been described on the order of 0.01 to 0.0462. In comparison, Teflon® on Teflon® has a coefficient of friction of 0.0463. The extremely low coefficient of friction values for cartilage have been explained through the biphasic response under loading. Under compression, the fluid pressurization and fluid flow out of the tissue forms a fluid film layer that dramatically decreases the coefficient of friction. However when cartilage was slid against a single phasic surface such as stainless steel with a continual static load, the tissue cannot rehydrate. Cartilage was tested against both cartilage and steel for continuous static loading, and the coefficient of friction for cartilage against a steel surface was low initially but increased under continual static loading. After long periods of time where the fluid pressurization has equilibrated, the final stage of lubrication is boundary lubrication. While this provides insight into the mechanism of cartilage tribology, physiological joint loading rarely occurs by a constant static loading.

As interstitial fluid pressurization and fluid flow contribute to the low coefficient of friction values observed in cartilage, it would be expected that the ion phase which increases the interstitial fluid pressurization through the Donnan osmotic pressure would affect resulting coefficient of friction values. The effect of the ion phase on the friction coefficient was confirmed by measuring the friction properties under different salt concentrations. In this test, the higher salt concentration bathing solutions resulted in lower interstitial fluid pressurization. The minimum and equilibrium friction coefficient decreased when the bath salt concentration increases. Thus, upon compressive loading of cartilage, at short time intervals the loading is supported by the fluid producing very low coefficient of friction values.

Despite the extensive study that has been done to understand the structure and properties of cartilage, there still remains a need in the art for a synthetic alternative to natural cartilage. The present disclosure is directed to this need.

Due to the importance of cartilage and the impact its loss has on individuals singly and societies collectively, attempts have been made to provide tissue replacements. However, these have various failings that limit their usefulness. For instance, Choi, J., Kung, H. J., Macias, C. E. & Muratoglu, O. K. Highly lubricious poly(vinyl alcohol)-poly(acrylic acid) hydrogels, J. Biomed. Mater. Res. B. Appl. Biomater. 524-532 (2011). Choi teaches a method for a physically cross-linked poly(vinyl alcohol) (PVA) hydrogel that has a reduced coefficient of friction by the addition of a linear anionic polymer, polyacrylic acid (PAA), into the PVA hydrogels. This strategy was then combined with PEG immersion before dehydration and annealing to prevent pore collapse. However, the Choi disclosure, unlike the current disclosure, fails to disclose a second hydrogel network synthesized with an anionic hydrogel. Further, Choi requires a separate PEG doping step to protect its porous structure and shows a significant drop in compressive strength.

Work done by Muratoglu, PVA hydrogels having improved creep resistance, lubricity, and toughness, U.S. Pat. Pub. No. 2010/0210752, Apr. 23, 2008, discloses a method for making double network hydrogels comprising physically cross-linked PVA and chemically crosslinking polyacrylamide (PAAm). These hydrogels are intended to demonstrate improved creep resistance, lubricity, and toughness. The disclosure explains its hydrogels have increased water content after annealing due to reduction in pore collapse. However, Muratoglu discloses a cationic gel for its ionic hydrogel component, whereas the current disclosure may utilize anionic hydrogels to serve as the GAG component of cartilage. Muratoglu et al. teaches the modification of charge density of sulfonated polymeric components through the variation in pH, which results in varying degrees of protonation of sulfate groups. However, Muratoglu et al. fails to disclose how charge density of the secondary anionic polymer component can be tailored through modification of chemical composition to mimic the charge density of GAG, as observed in natural cartilage.

In another reference, Highly Porous Polyvinyl Alcohol Hydrogels For Cartilage Resurfacing, WO 2012/118662, a method is described for synthesizing a creep resistant, highly lubricious, tough hydrogel. The method describes a solution of a first polymer and polyacrylamide-co-acrylic acid as a second polymer. A second solution is added to gelate the first solution into a hydrogel. The formation of the first hydrogel network is taught to occur by ionic gelation. The first polymer, e.g., PVA, is then disclosed to be physically cross-linked through freeze-thaw cycles. However, this disclosure is directed to a combination of a physically cross-linked hydrogel and an ionically cross-linked hydrogel. An ionically cross-linked hydrogel will differ from those of the present disclosure because the charge units along the side of the polymer chain are used to crosslink the polymer. The disclosed hydrogels will possess internal ionic bonding rather than being chemically cross-linked.

U.S. Pat. Pub. No. 2011/0054622, discloses a method for synthesizing polymer networks with a physically cross-linked polymer and a chemically cross-linked ionic polymer network. The reference discloses PVA as the physically cross-linked component and polyacrylamido-methylpropane sulfonic acid (PAAMPS) as the ionic gel component. The PAAMPS component provides an anionic charge in the form of sulfate groups. Ionic or monomeric compounds may be mixed with a hydrogel to impart ionic properties that can be used to increase the water uptake of the host hydrogel. However, the reference is silent as to selectively engineering each component of a synthetic tissue to mimic the function of the different components of cartilage. Thus, using the disclosed replacement material would not closely mimic the characteristics of natural cartilage. Indeed, this reference is silent as to how one skilled in the art would design a cartilage substitute that matches the mechanical properties while mimicking tribological properties. For example, the reference is silent on specifications for Young's modulus, aggregate modulus, Poisson's ratio, fixed charge density, coefficient of friction, and hydraulic permeability. In addition, this prior art is specific on mixing pre-gelled solutions with PVA solutions. This prior art is silent on how one skilled in the art might react the chemically cross-linked network with the PVA in order to have both a homogenous chemically crosslinked network and physically crosslinked PVA hydrogel.

See also, for example: Cheng, Y. et al, *Morb. Mortal. Wkly. Rep.* 2010, 59 (39), 1261-126; Kotlarz, H. et al., *Arthritis Rheum.* 2009, 60 (12), 3546-3553; Blagojevic, M.

et al., *Osteoarthr. Cartil.* 2010, 18 (1), 24-33; Rossignol, M. et al., *Occup. Environ. Med.* 2005, 62 (11), 772-777; Murphy, L. et al., *Arthritis Rheum.* 2008, 59 (9), 1207-1213; Porcheret, M. et al., *Rheumatology* (Oxford). 2007, 46 (4), 638-648; Taljanovic, M. S. et al., *Radiographics* 2003, 23 (5), 1295-1314; Bozic, K. J. et al., *Clin. Orthop. Relat. Res.* 2010, 468 (1), 45-51; Kurtz, S. M. et al., *Clin. Orthop. Relat. Res.* 2009, 467 (10), 2606-2612; Barrack, R. L. et al., *J. Arthroplasty* 1995, 10 (3), 281-286; Fitzgerald, S. J.; Trousdale, R. T. *Orthopedics* 2011, 34 (9), e513-e515; Rossi, M. D. et al., *Orthopedics* 2009, 32 (12), 885; Cicuttini, F. M. et al., *Ann. Rheum. Dis.* 2004, 63 (9), 1124-1127; Sciarretta, V.; Nostra, C. *Eur. Rev. Med. Pharmacol. Sci.* 2013, 17, 3031-3038; Mescher, A. L. *Junqueira's basic histology: text & atlas*; McGraw-Hill Medical New York, 2010; Vol. 12; Guilak, F. et al., *J. Orthop. Res.* 1994, 12 (4), 474-484; Setton, L. A. et al., *Osteoarthr. Cartil.* 1999, 7 (1), 2-14; Setton, L. A. et al., *Clin. Orthop. Relat. Res.* 1999, 367, S254-S272; Fox, A. J. S. et al., *Sports Health* 2012, 4 (4), 340-351; Setton, L. A., *Eur. Cells Mater.* 2005, 10 (SUPPL.3), 22; Mow, V. C. et al., *Biomaterials* 1992, 13 (2), 67-97; Mansour, J. M. Biomechanics of Cartilage. In *Kinesiology: the mechanics and pathomechanics of human movement;* 2003; pp 66-79; Lai, W. M. et al., *J. Biomech. Eng.* 1991, 113 (3), 245-258; Mow, V. C. et al., *J. Biomech. Eng.* 1980, 102 (1), 73-84; Eyre, D., *Arthritis Res.* 2002, 4 (1), 30-35; Fox, A. J. S. et al., *Sports Health* 2009, 1 (6), 461-468; Buckley, M. R. et al., *J. Biomech.* 2008, 41 (11), 2430-2437; Kempson, G. E., *Biochim. Biophys. Acta (BBA)—General Subj.* 1991, 1075 (3), 223-230; Eleswarapu, S. V. et al., *PLoS One* 2011, 6 (10), e26178; Williamson, A. K. et al., *J. Orthop. Res.* 2003, 21 (5), 872-880; Eyre, D. R. et al., *FEBS Lett.* 1987, 220 (2), 337-341; Maroudas, A., *Nature* 1976, 260 (5554), 808-809; Watanabe, H. et al., *J. Biochem.* 1998, 124 (4), 687-693; Maroudas, A., *Adult Articul. Cartil.* 1979, 2, 215-290; Mow, V. C. et al., *Int. J. Solids Struct.* 1998, 35 (98), 4945-4962; Katta, J. et al., *Proc. Inst. Mech. Eng. H.* 2008, 222 (1), 1-11; Mankin, H. J. et al., *J. Boneit. Surg.* 1975, 57(1), 76-80; Armstrong, C. G.; Mow, V. C., *J. Bone Jt. Surg.* 1982, 64 (1), 88-94; Zhang, L. et al., *Crit. Rev. Biomed. Eng.* 2011, 37 (530), 1-44; Chen, A. C. et al., *J. Biomech.* 2001, 34 (1), 1-12; Camacho, N. P. et al., *Biopolymers* 2001, 62 (1), 1-8; Kempson, G. E. et al., *Biochim. Biophys. Acta (BBA)—General Subj.* 1973, 297 (2), 456-472; Boschetti, F. et al., *Biorheology* 2004, 41 (3-4), 159-166; Roth, V.; Mow, V. C., *J. Bone Jt. Surg.* 1980, 62 (7), 1102-1117; Mow, V. C.; Lai, W. M., *SIAM Rev.* 1980, 22 (3), 275-317; Lu, X. L.; Mow, V. C., *Med. Sci. Sports Exerc.* 2008, 40 (2), 193-199; Mow, V. C.; Huiskes, R. *Basic orthopaedic biomechanics & mechano-biology*; Lippincott Williams & Wilkins, 2005; Mak, A. F., *Biorheology* 1985, 23 (4), 371-383; Cohen, B. et al., *J. Biomech. Eng.* 1998, 120 (August 1998), 491-496; Spilker, R. L. et al., *J. Biomech.* 1992, 25 (9), 1027-1045; Armstrong, C. G. et al., *J. Biomech. Eng.* 1984, 106 (2), 165-173; Mow, V. C. et al., *J. Biomech.* 1989, 22 (8), 853-861; Sun, H. B., *Ann. N. Y. Acad. Sci.* 2010, 1211, 37-50; Lee, A. S. et al., *Gene* 2013, 527 (2), 440-447; Troeberg, L. et al., *Biochim. Biophys. Acta* 2012, 1824 (1), 133-145; Bell, C. J. et al., *Proc. Inst. Mech. Eng. H.* 2006, 220, 23-31; Forster, H.; Fisher, J., *Arch. Proc. Inst. Mech. Eng. Part H J. Eng. Med.* 1989-1996 (v. 203-210) 1996, 210 (28), 109-119; Forster, H.; Fisher, J., *Proc. Inst. Mech. Eng. H.* 1999, 213 (4), 329-345; Krishnan, R. et al., *J. Biomech.* 2005, 38 (8), 1665-1673; Katta, J. et al., *Med. Eng. Phys.* 2008, 30 (10), 1349-1363; Unsworth, A. et al., *J. Lubr. Technol.* 1975, No. July, 369-376; McCutchen, C. W., *Nature* 1959, 184, 1284-1285; McCutchen, C. W., *Wear* 1962, 5 (1), 1-17; Ateshian, G. A., *J. Biomech.* Eng. 1997, 119 (February), 81-86; Ateshian, G. A. et al., *Transp. Porous Media* 2003, 50 (1-2), 5-33; Oka, M. et al., *Clin. Mater.* 1990, 6, 361-381; and Oka, M. et al., *Proc. Inst. Mech. Eng. Part H-Journal Eng. Med.* 2000, 214, 59-68.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

In brief, the present disclosure provides double network (DN) hydrogels, methods of making the hydrogels and methods of using the hydrogels. For example, in one embodiment the present disclosure provides a double network hydrogel comprising two separate polymeric components, the first component comprising a chemically cross-linked anionic polymer and the second component comprising a physically cross-linked poly(vinyl alcohol). In additional embodiments, the present disclosure provides a double network hydrogel comprising a first network and a second network, the first network is or comprising a first polymer comprising —$CH_2$—CH(OH)— units; the second network is or comprising a second polymer comprising carboxyl (COOH)-containing units or salts thereof, sulfonyl ($SO_3H$)-containing units or salts thereof, and at least one of hydroxyl (OH)-containing units or amino ($NH_2$)— containing units.

In exemplary embodiments, the DN hydrogels of the present disclosure may optionally be further described by any one or more (for example, two, three, four, five, six, etc.) of the options described herein, including the following: the first polymer is polyvinyl alcohol; the first polymer is a copolymer that includes —$CH_2$—CH(OH) units; the carboxyl-containing units are derived from a monomer selected from acrylic acid (AA) and methacrylic acid (MA); the sulfonyl-containing units are derived from a monomer selected from 3-sulfopropyl methacrylate, 3-sulfopropyl acrylate, 2-sulfoethyl methacrylate, 2-propene-1-sulfonic acid, and 2-acrylamido-2-methylpropane sulfonic acid (AMPS); the amino-containing units are derived from acrylamide (AAm); the hydroxyl-containing units are derived from a monomer selected from N-(tris(hydroxymethyl)methyl)acrylamide and N-hydroxyethyl acrylamide; the first polymer is polyvinyl alcohol and the second polymer is formed from monomers including each of AA, AMPS and AAm; the first polymer is made from x moles of monomer(s) and the second polymer is made from y moles of monomer(s), and x/(x+y) is at least 0.7, or at least 0.75, or at least 0.8, or at least 0.85, or at least 0.9, or at least 0.95; the first network is semi-interpenetrated with the second network; the first network is physically crosslinked; the first network is physically crosslinked by multiple freeze thaw cycles; the second network is chemically crosslinked; the second network is chemically crosslinked with N,N'-methylenebisacrylamide (MBAA); the second polymer comprises crosslinking units derived from a crosslinking agent, and the crosslinking agent provides not more than 2.5 molar units when the carboxyl (COOH)-containing units or salts thereof, the sulfonyl (SO$_3$H)-containing units or salts thereof, the at least one of hydroxyl (OH)-containing units or amino (NH$_2$)-containing units, and the crosslinking units provide a total of 100 molar units; the hydrogel is in the form of a hybrid double network hydrogel wherein the first network is physically crosslinked and the second network is chemically crosslinked.

In another embodiment the present disclosure provides a composition that comprises a DN hydrogel as described herein, and water, optionally water in the form of saline or optionally aqueous PBS buffer. Optionally, the composition is sterile. Optionally, the composition exhibits a poroelastic response.

In another embodiment, the present disclosure provides a polymer that may be used to prepare a DN hydrogel of the present disclosure. For example, the present disclosure provides a polymer prepared from the monomers acrylic acid (AA), acrylamide (AAm), 2-acrylamido-2-methylpropane sulfonic acid (AMPS) and a crosslinking agent. Optionally, the monomers constitute 50-75 wt % AA, 10-35 wt % AMPS and 5-25 wt % AAm, the sum of the monomer weight percentages equaling 100. Optionally, the crosslinking agent is N,N'-methylenebisacrylamide (MBAA).

In one embodiment, the present disclosure provides a method of improving an animal joint where the joint comprises cartilage, the method comprising placing a DN hydrogel of the present disclosure in the joint to provide a synthetic cartilage for the joint. In this regard, it is noted that in 2010, over 700,000 total knee replacements (TKR) were performed in the United States with nearly half of these operations conducted on patients under the age of 65 years old. Currently, limited treatment options are available for patients 40-65 years old living with joint pain. Specifically microfracture, which is the standard of care for repairing cartilage lesions, is less effective in patients over 40 years old and especially ineffective in arthritic joints. The present disclosure provides for relieving joint pain through the use of a synthetic cartilage substitute for implanting in place of diseased cartilage tissue. In particular, the present disclosure provides DN hydrogels that have the same foundational loading mechanisms as cartilage, thus making them particularly well suited as cartilage substitutes.

In this regard, the DN hydrogels useful as an articular cartilage mimetic respond to compressive loading similar to how the biphasic and triphasic theory describes articular cartilage loading and unloading. In one embodiment, the DN hydrogels of the present disclosure include a physically cross-linked PVA-only hydrogel that has a desired porosity in order to elicit a poroelastic response. In combination with a network consisting of this PVA-only hydrogel, the present disclosure adds an additional network formed from an anionic chemical cross-linked polymer in order to add pore stability and to mimic the functionality of glycosaminoglycans (GAG) in native cartilage.

The pore size and relative porosity of PVA-only hydrogels may be modulated by modifying the freezing rate, number of freeze/thaw cycles and concentration of aqueous PVA. The present disclosure provides DN hydrogels which incorporate the physically crosslinked PVA-only hydrogels with an additional network of chemically cross-linked anionic copolymers. The composition of the DN hydrogels may be varied by changing the PVA to anionic copolymer ratio, concentration of cross linker, and composition of anionic copolymer. Upon synthesis of these compositions, the PVA double network hydrogels were analyzed to determine the effect of anionic copolymer composition on compressive modulus, Poisson's ratio, water content, relative crystallinity, degree of swelling, and free swelling diffusion coefficient.

The above-mentioned and additional features of the present invention and the manner of obtaining them will become apparent, and the invention will be best understood by reference to the following more detailed description. All references disclosed herein are hereby incorporated by reference in their entirety as if each was incorporated individually This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings. One or more embodiments are described hereinafter with reference to the accompanying drawings in which:

FIG. 7 shows formulations of PVA Double Network Hydrogels.

FIG. 8, meanwhile, shows properties of PVA Double Network Hydrogels.

(FIG. 9A) and thawed at 20° C.

FIG. 11A-D show the following perspective of cylindrical molded PVA hydrogels: FIG. 11A: bottom, FIG. 11B: top, FIG. 11C: side, and FIG. 11D: cross-section.

FIG. 12A: image with −80° C. freezing; 2.73° C./min freezing rate, FIG. 12B: image with −20° C. freezing temperature; $7.89\times10^{-2\circ}$ C./min freezing rate, FIG. 12C pore size distribution at −80° C. freezing, FIG. 12D pore size distribution at −20° C. freezing.

FIG. 13 shows a table illustrating the effect of effect of freeze rate and concentration on the mechanical properties of PVA Hydrogels of the current disclosure.

FIG. 14 shows a table illustrating the effect of freeze rate and concentration on the water volume fraction and percent crystallinity of PVA hydrogels of the current disclosure.

FIG. 20B: DNH 4 versus a 20% PVA control (mean±standard deviation, n=3).

FIG. 21B: median qualitative scoring for cytotoxicity (mean±standard deviation, n=5).

Figure 1:
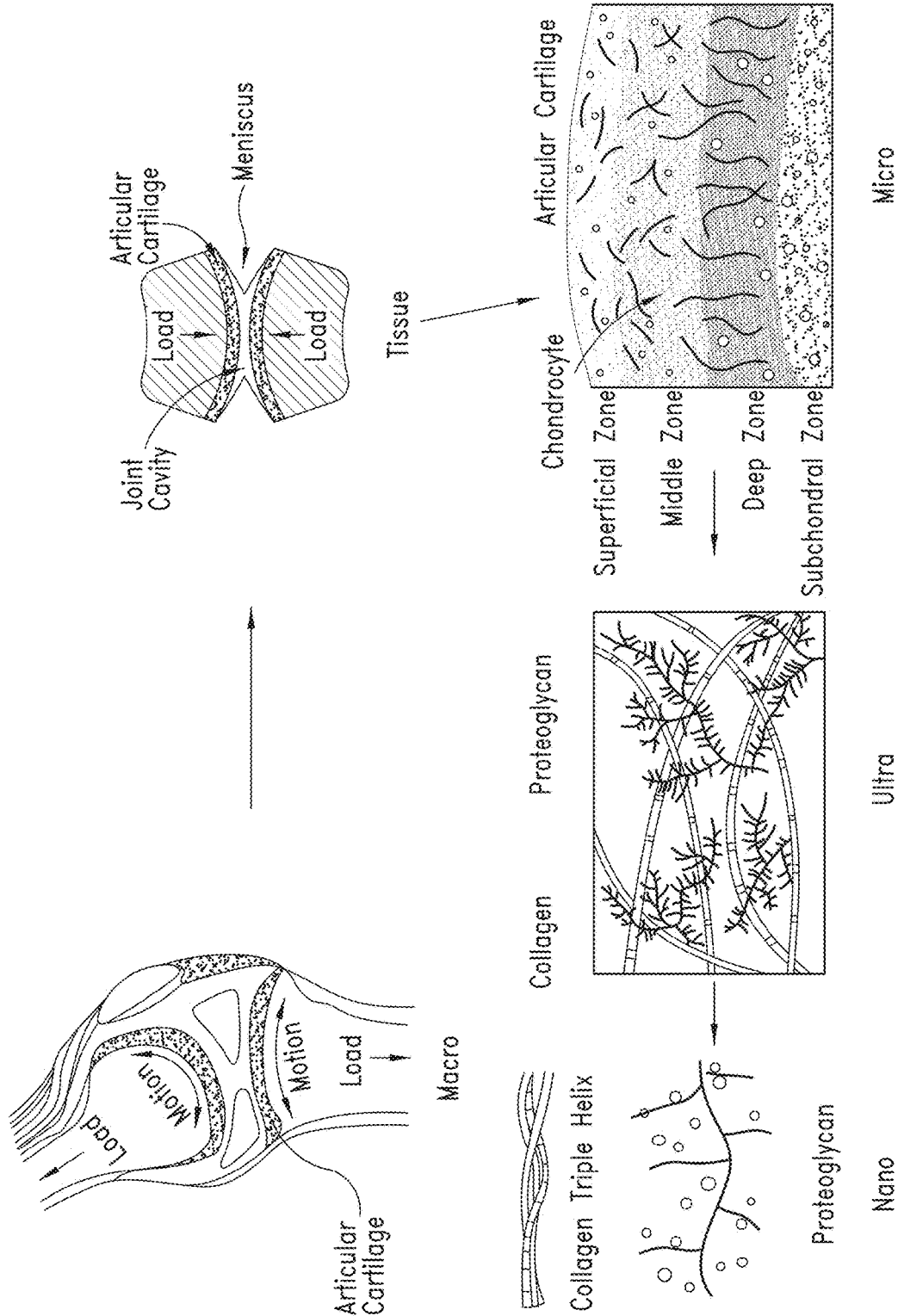
FIG. 1 shows the structure of cartilage from macro to microscale.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

The construction designed to carry out the invention will hereinafter be described, together with other features thereof. The invention will be more readily understood from a reading of the following specification and by reference to the above-mentioned drawings forming a part thereof.

DETAILED DESCRIPTION OF THE INVENTION

With reference to the drawings and the Examples, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

As referred to herein, a biocompatible material is one that is capable of performing its desired function without causing harm to the living tissue. A biostable material is a biomaterial that keeps its original mechanical, chemical, and physical properties throughout an implantation period. In orthopedic applications, the biocompatibility and biostability are closely related as materials must maintain certain mechanical functionality while minimizing material degradation and wear that can result in an undesired tissue response. Therefore, developing materials for cartilage replacement applications not only focuses on initial biocompatibility but tissue response after long term application.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Some specific double network hydrogels described in this disclosure are identified under the sample names of DN #and DNH #as abbreviations.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

In one embodiment the present disclosure is direct to a material for double network hydrogels that is synthesized to mimic the intrinsic properties of soft tissue such as cartilage. A double network hydrogel may be formed that may be comprised of two separate polymeric components. The first component may be a chemically cross-linked anionic copolymer. For example, the anionic copolymer may be comprised of monomers with carboxyl and sulfate moieties. Some examples of the anionic copolymers are poly(acrylic acid-co-2-acrylamido-2-methyl-1-propanesulfonic acid), poly(methacrylic acid-co-2-acrylamido-2-methyl-1-propanesulfonic acid), poly(acrylic acid-co-2-acrylamido-2-methyl-1-propanesulfonic acid-co-acrylamide), poly(acrylic acid-co-vinylsulfonic acid), poly(methacrylic acid-co-vinylsulfonic acid), and poly(methacrylic acid-co-vinylsulfonic acid-co-acrylamide). In one embodiment the copolymer composition will be tuned to have a fixed charge density similar to articular cartilage. The second component may be a physically cross-linked poly(vinyl alcohol) (PVA). The invention may comprise PVA and PVA copolymers with PVA as the major component of the physically cross-linked polymer. In a preferred embodiment, the physically cross-linked polymer consists of a PVA homopolymer in order to maximize hydrogen bonding and resulting crystallinity. In some situations, the incorporation of a secondary component in addition to PVA may serve to weaken the physically cross-linked hydrogel by reducing the degree of hydrogen bonding between the PVA homopolymer or copolymer thereof.

One of the main challenges in designing a cartilage substitute is matching the mechanical properties (for example, aggregate modulus) while also mimicking the tribological properties (for example, coefficient of friction). Additional relevant properties include specifications for Young's modulus, aggregate modulus, Poisson's ratio, fixed charge density, coefficient of friction, and hydraulic permeability. Specifications for each of these intrinsic properties are needed or may be used to begin to tailor a double network hydrogel's mechanical properties to a desired tissue. For example, for a cartilage substitute, the aggregate modulus should range from 0.25 MPa to 1.3 MPa, Poison's ratio should range from 0.06 to 0.45, the coefficient of friction ranges from 0.001 to 0.20, and the hydraulic permeability should range between $10^{-13}$ to $10^{-16}$. In one embodiment, the DN hydrogels of the present disclosure provide one or more of these properties.

One improvement in the synthesis of the double network hydrogels is increasing the freeze cycle rate of the double network hydrogel. This can be completed by using a mold consisting of half metal and half glass and increasing the freezing temperature. The metal portion of the mold can aid in increasing the freezing rate of the freeze cycles. The change will allow for a decrease in the ice crystal size. Therefore the pore size in the PVA hydrogels will be decreased. This modification will allow for fine tuning the hydraulic permeability and Poisson's ratio.

In one embodiment, the present disclosure provides novel physically cross-linked PVA hydrogels via the incorporation of a chemically cross-linked anionic gel component that is modified to mimic the intrinsic mechanical properties of soft tissue, such as cartilage along with its tribological functionality. With respect to forming a synthetic cartilage, this may be accomplished by designating PVA as the major solid elastic portion of cartilage, which in turn will mimic collagen. The anionic hydrogel component will mimic the glycosaminoglycan (GAG) component that adds a negative charge to cartilage along with lubricity. This may be accomplished in a two-step reaction procedure wherein a PVA homopolymer or copolymer is dissolved in water. After PVA dissolution, the temperature is reduced. The anionic monomers are first added neat and dissolved into the PVA aqueous solution for a homogeneous mixture of monomer and PVA. Then, the free radical initiator, and cross-linker are added to the PVA solution and dissolved. The solution is then cast into a mold. The anionic monomers in the solution are reacted by free radical polymerization. The freeze thaw cycles are then conducted on the mold. The double network hydrogels are synthesized under a fast freeze rate and slow thaw cycle.

With respect to mimicking cartilage, the concentration of collagen and GAG vary with respect to the location of cartilage within the body. With insight into these concentrations along with the mechanical and tribological properties of the cartilage unique to those locations, the present disclosure may be used to mimic cartilage in any location of the body. As the composition, concentration, and processing of the double network hydrogel is modified, the biphasic and triphasic theories are used to establish the intrinsic mechanical properties for the double network hydrogel and compared to articular cartilage.

The present disclosure is also novel due to physically cross-linked PVA hydrogels with the incorporation of a chemically cross-linked anionic gel component comprising carboxyl/carboxylic acid, sulfate/sulfonic acid, cationic, and non-ionic groups to more closely mimic the contribution of GAG in cartilage. This portion of the disclosure focuses on synthesizing an anionic hydrogel component in the double network hydrogel that may have a fixed charge density, the measure of electric charge per unit volume of space, which closely mimics cartilage. In order to do this, monomer composition and concentration may be varied to formulate a hydrogel network to meet similar fixed charge densities of cartilage. The monomers may comprise carboxyl/carboxylic acid, sulfate/sulfonic acid, non-ionic, and cationic groups.

In a further embodiment, the present disclosure describes distinct compositions and concentrations of monomers, free radical initiators and cross-linkers for anionic hydrogels. The PVA hydrogel component may be varied based on its molecular weight, concentration, number of freeze thaw cycles, annealing temperature, annealing time, and freeze-thaw rate, amongst other possible features that may be tailored to produce a synthetic soft tissue.

In a further embodiment, each component of the double network hydrogel may be designed to describe one of the three phases of articular cartilage—a viscous fluid phase, an elastic solid phase, and an ionic phase. Water may be the major component of the viscous fluid phase. PVA may serve as the major component of the elastic solid phase, which is normally collagen. An anionic hydrogel may serve as a minor component of the solid phase which may be glycosaminoglycans (GAG). Additionally, the anionic hydrogel represents the charged component, which may be the GAG, and may have a fixed charge density. This component may allow for osmotic pressure differences that are described as the ion phase in the triphasic theory. The composition of the anionic hydrogel may be synthesized to mimic fixed charge density of the GAG component in in vivo conditions.

As described herein, prior efforts have failed to engineer each chemical component of synthetic soft tissue to function as a different component of cartilage. Therefore, the past work would not lead to forming a material that functions as effectively as the present disclosure with respect to mimicking cartilage. Each component may first be designed and then described in regards to how it will act as a functional component of cartilage. The individual components collaboratively function to mimic in vivo tissue, especially the individual chemical components of the hydrogels. What is needed, and is herein disclosed, is a cartilage substitute material that mimics both the mechanical and tribological functionality of in vivo cartilage. In a further embodiment, the ionic gel component is formulated to have a similar charge density to GAG. In a further embodiment, a soft tissue replacement is provided that may be made from monomer compositions and concentrations along with specifications for fixed charge density to mimic the charged properties of GAG.

In one embodiment, the composition of the double network hydrogels may be comprised of physically cross-linked PVA as the major solid component, water as the major fluid component, and anionic hydrogels as the charged anionic hydrogel component. These double network hydrogels are synthesized in an aqueous solution of PVA, anionic monomer, cross-linker, and free radical initiator. After an aqueous, homogenous solution containing these components is formed, the solution is cast into a mold. The anionic monomers, cross-linker and initiator may be reacted to create a chemically cross-linked anionic hydrogel network with the linear PVA encapsulated within the network. This semi-IPN of anionic hydrogel and linear PVA is freeze-thawed to physically crosslink the PVA component. The final result after multiple freeze thaw cycles is a double network hydrogel comprising of physically cross-linked PVA and an anionic hydrogel network. The physical cross-linking of the PVA hydrogel component results in a porous hydrogel that allows for water fluid flow within the polymer network. The physically cross-linked PVA is an elastic solid, and water within the hydrogel acts as a viscous component. As the double network hydrogel is compressed, the material acts as a viscoelastic solid. Additionally, frictional drag forces arise from the interface between the solid elastic component and viscous liquid component. The anionic hydrogel provides a charged component within the physically cross-linked PVA hydrogel. This charge will affect the ion flow in and out of the hydrogel and is described by the Donnan osmotic pressure. The overall effect of the anionic hydrogel can be modelled under the triphasic theory to determine the fixed charge density. Further, processing of the double network hydrogel may involve dehydration and annealing, but these steps are not essential in some embodiments.

This system allows for a high degree of modularity which is due to synthesis of hydrogel networks by both physical and chemical cross-linking mechanisms. PVA hydrogel's mechanical properties may be modulated through weight percent PVA, molecular weight of PVA, degree of hydrolysis, number of freeze-thaw cycles, annealing temperature, annealing time, and freeze/thaw rate. The anionic hydrogel may be modified through anionic monomer composition, anionic monomer concentration, cross-linker concentration, cross-linker composition, reaction time, free radical initiator composition, and free radical initiator concentration. Due to the high modularity in double network hydrogel systems, detailed formulations are needed to derive a composition that mimics the intrinsic mechanical properties and tribological functionality of cartilage.

In a further embodiment, in the chemically cross-linked ionic hydrogels, the charged functional groups do not form ionic bonds with each other; instead, they are intended to exist as un-bound, charged side groups that can draw water into the construct from the surrounding environment, which creates osmotic pressure in the double network hydrogels.

In a further preferred embodiment, initial specifications for construction of the double network hydrogels needed to match the intrinsic mechanical and tribological functionality of cartilage may be described as follows. The PVA hydrogel component may have a molecular weight of greater than 60 kiloDaltons (kDa), preferably 60-200 kDa, more preferably 100-200 kDa, and even more preferably 140-500 kDa, and even more preferably >140 kDa. The degree of hydrolyzation of the PVA hydrogel component may be greater than 90%, more preferably from 90% to 99%, even more preferably greater than 98%, and even more preferably greater than 98.5%. The concentration of the PVA may be greater than 10%, greater than 15%, and even more preferably from 15-40% measured by mass of initial charge, preferably from 15% to 25%, and more preferably greater than or equal to 25%, and even more preferably from 25% to 40%. The number of freeze-thaw cycles may also be manipulated to modify the characteristics of the hydrogel. The number of freeze thaw cycles may be greater than 1, more preferably greater than 3 and even more preferably from 9 to 20. The polymer solutions may be cast into a mold constructed of glass, metal or any combination thereof. The mold may be placed in a freezer at a minimum of −5° C., preferably a minimum of −20° C., and more preferably between −60 to −80° C. The polymer solution may be frozen from a minimum of 1 hour and more preferably a minimum of 3 hours. The polymer solution may be subsequently thawed at a rate of 0.01 to 10° C./min, in a further embodiment, the thaw rate may be <1° C./min. The freeze thaw step may be repeated for addition cycles. In one embodiment, more than one freeze thaw cycle is used, in a further embodiment, preferably more than 3 freeze thaw cycles may be employed. In a still further embodiment, from 9-15 freeze thaw cycles may be employed. An increasing number of freeze thaw cycles may result in more crystallinity of the physically cross-linked hydrogel. This may give the physically cross-linked hydrogel more stability and may increase the modulus of the PVA-based hydrogel. In one embodiment, the effects of the freeze thaw cycles may plateau at around 10 freeze thaw cycles.

Thaw rate may also be manipulated to control the crystallinity of the hydrogel. In a still further embodiment, the thaw rate may be less than 0.5° C./min, preferably less than 0.1° C./min, and even more preferably less than 0.01° C./min, and even more preferably less than 0.008° C./min.

In one embodiment, the PVA double network hydrogel is synthesized by the dissolution of PVA into water or saline at a temperature greater than 80° C. and more preferably greater than 90° C.

The anionic hydrogel component may also be engineered to provide a synthetic soft tissue replacement. The anionic monomer may be an acrylic monomer carboxyl/carboxylic acid moieties, such as acrylic acid, ethacrylic acid, methacrylic acid, 2-propyl acrylic acid, sodium acrylate, and sodium methacrylate, and sulfate/sulfonic acid moieties, such as 2-acrylamido-2-methyl-1-propanesulfonic acid, 2-acrylamido-2-methyl-1-propanesulfonic acid sodium salt, 4-styrenesulfonic acid sodium salt hydrate and vinyl sulfonic acid. In a further embodiment, the concentration of carboxyl/carboxylic acid bearing monomers may be 1%-80%, more preferably 20%-80% and even more preferably 40-80%, measured by mole percent of initial charge. In a still further embodiment, the concentration of sulfate/sulfonic acid bearing monomers may be 1%-80%, more preferably <40% and even more preferably <25%, measured by mole percent of initial charge. One advantage of the specific formulations outlined herein is the capability for tailoring the monomer charge to achieve a set fixed charge density, Young's modulus, coefficient of friction, and percent crystallinity from the PVA component.

In a further embodiment, non-ionic and cationic monomers may be employed. This may include dimethacrylamide, diacetone acrylamide, n-tert-butylacrylamide, alkylacrylamide, N-[tris(hydroxymethyl)methyl]acrylamide, n-hydroxyethyl acrylamide, n-(hydroxymethyl) acrylamide, n-isopropyl acrylamide, methacrylamide, propyl vinyl ether, phenyl vinyl ether, isobutyl vinyl ether, ethyl vinyl ether, ethyl-1-propyl vinyl ether, 2-thylhexyl vinyl ether, ethylene glycol vinyl ether, diethyl vinyl orthoformate, di(ethylene glycol) vinyl ether, cyclohexyl vinyl ether, 1,4-butanediol vinyl ether, butyl vinyl ether, ethyl vinyl sulfide, and mixtures thereof. In a further embodiment, the concentration of non-ionic monomers may be from 1%-60% and preferably 10-60%, measured by mole percent of initial charge. One advantage of the specific formulations outlined herein is the capability for tailoring the monomer to achieve a set fixed charge density, Young's modulus, and percent crystallinity from the PVA component. Some of the non-ionic monomers may degrade to form anionic repeat units upon degradation. This may include methyl acrylate, methyl methacrylate, 2-(diethylamino)ethyl acrylate, ethyl acrylate, ethyl methacrylate, ethyl propylacrylate, ethyl ethylacrylate, ethylhexyl acrylate, polyethylene glycol methyl ether acrylate, hexyl acrylate, octodecyl acrylate, 2-(diethylamino)ethyl acrylate, 2-(Dimethylamino)ethyl acrylate, propyl acrylate, butyl acrylate, tert-butyl acrylate or mixtures thereof. Some of the cationic monomers may degrade to form anionic repeat units upon degradation. This may include, [2-(acryloyloxy)ethyl]-trimethylammonium chloride.

Suitable crosslinkers may include acrylamides, such as methylene bisacrylamide and vinyl compounds, such as divinylbenzene, 1,4-butanediol divinyl ether, and di(ethylene glycol) divinyl ether. In one embodiment, cross linker concentration, measured by mole percent relative to total moles of monomer, may be less than 10%, from 10% to 4%, and more preferably less than 4%, even more preferably less than 2%, and still even more preferably less than 1% measured by mole percent of initial charge. One advantage of the specific formulations outlined herein is the capability for tailoring the monomer to achieve a set fixed charge density, Young's modulus, and percent crystallinity from the PVA component.

In a further embodiment, initiators may be used. These may include nitriles, such as azobisisobutyronitrile, peroxides, such as benzoyl peroxide, and photoinitiators, such as Irgacure 2959. Specific initiators may include but are not limited to 1,1-azobisisobutyronitrile, azobis(cyclohexanecarbonitrile), 2,2-azobis(methylpropionamidine) dihydrochloride, and 2,2-azobis(methylpropionitrile), inorganic peroxides, such as ammonium persulfate, hydroxymethanesulfinic acid monosodium salt dehydrate, potassium persulfate, and sodium persulfate, organic peroxides, such as benzoyl peroxide, tert-butyl hydroperoxide, tert-butyl peracetate, cumene hydroperoxide, dicumyl peroxide, 2,5-di(tert-butylperoxy)-2,5-dimethyl-3-hexyne, Luperox® 101, Luperox® 224, Luperox® 231, Luperox® 331M80, Luperox® 531M80, Luperox® DDM-9, Luperox® DHD-9, Luperox® LP, Luperox® P, Luperox® TBEC, and Luperox® TBH70X, and photoinitiators, such as Irgacure 2959, Irgacure 500, Irgacure 754, Irgacure 1173, and Darcocur® MBF. In a still further embodiment, the initiator concentration, measure by mole percent relative to total moles of monomer, may be less than 3.0%, from 3.0% to 1.5%, and more preferably less than 1.5%, still even more preferably less than 1.0%, and even more preferably less than 0.5% but preferably greater than 0.1%.

In a further embodiment, the mass percent of PVA and chemically crosslinked network may include PVA greater than 50%, from 50% to 80%, more preferably greater than 80%, still further from 80% to 95% of the total polymer mass, measured by mass percent of initial charge. The percentage of the anionic component may be from 0.1 to 50%, more preferably less than 30%, even more preferably less than 15%, and even more preferably less than 10%, measured by mass percent of initial charge. The anionic monomer will preferably be reacted prior to the first freeze thaw cycle, but may be polymerized after 1-10 freeze thaw cycles.

In a further embodiment, after synthesis, the hydrogels may be dehydrated and annealed. The hydrogels may be dehydrated with heat, vacuum, freeze/dry or through solvent dehydration. Annealing temperatures may be greater than 100° C. and more preferably greater than 120° C. The annealing time may range from 0.5 to 4 hours. Annealing may be accomplished by placing the polymer between two glass or metal sheets and a metal spacer, 1 mm to 1 cm thick, and 100° C. to 120° C. Each of dehydration and annealing is, however, and optional step in preparing the DN (Double Network) hydrogels of the present disclosure.

In a further embodiment, a synthetic articular cartilage in the form of a DN hydrogel of the present disclosure may be produced that has one or more of the following properties. The articular cartilage may have a Young's Modulus (MPa) of 0.4 to 10 MPa, more preferably 0.4 to 2 MPa. The articular cartilage may have an Aggregate Modulus of 0.1 to 10 Mpa, more preferably 0.1 to 2 MPa. The synthetic articular cartilage may have a Hydraulic Permeability ($mm^4$/N*s) of $10^{-13}$ to $10^{-16}$ more preferably $10^{-14}$ to $10^{-16}$. The synthetic articular cartilage may have a fixed charge density (mEq/ml): from 0.01 to 3, more preferably from 0.04 to 2, and even more preferably from 0.0001 to 0.4. The equilibrium water content (%) may be 60-80 mass % water. In a further embodiment, the Coefficient of Friction may be from 0.005 to 0.57, more preferably from 0.005 to 0.1, measured via a rheometer. The synthetic articular cartilage may also have a water volume fraction (%) that ranges from 60% to 90%, preferably greater than 80%, more preferably greater than 70%, even more preferably greater than 60%, and even more preferably ranging from 60% to 90%. The water volume fraction is measured the direct method or similar methods used to determine apparent porosity (ASTM C20). Additionally, the synthetic articular cartilage may have a coefficient of friction from 0.005-0.57 and more preferably from 0.005-0.2.

Figure 2:
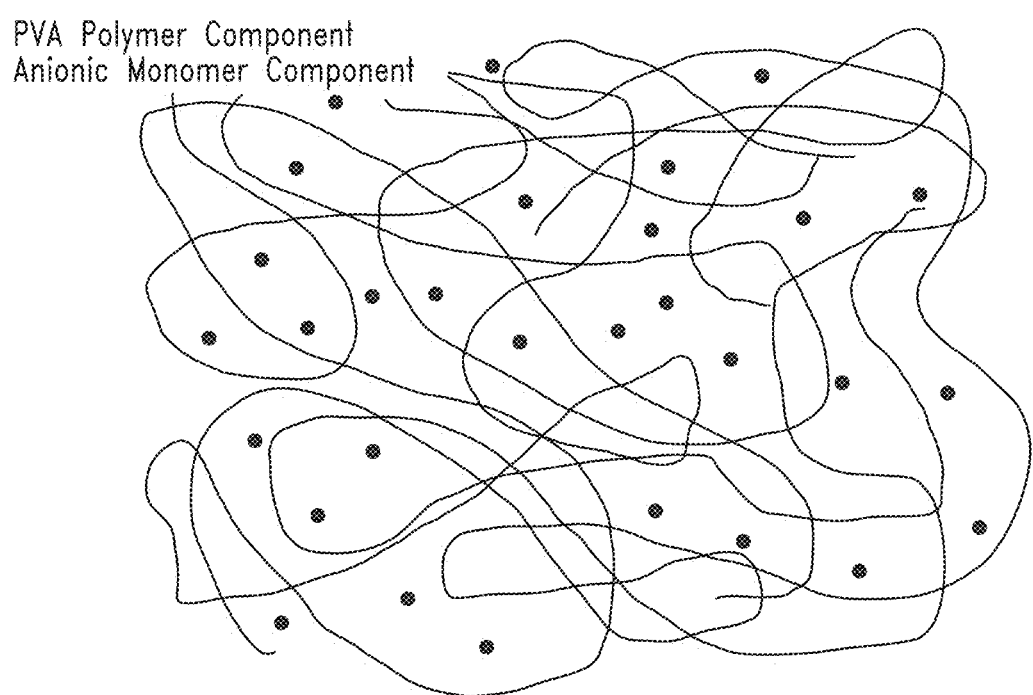
FIG. 2 shows an initial polymer/monomer solution in water.
Figure 3:
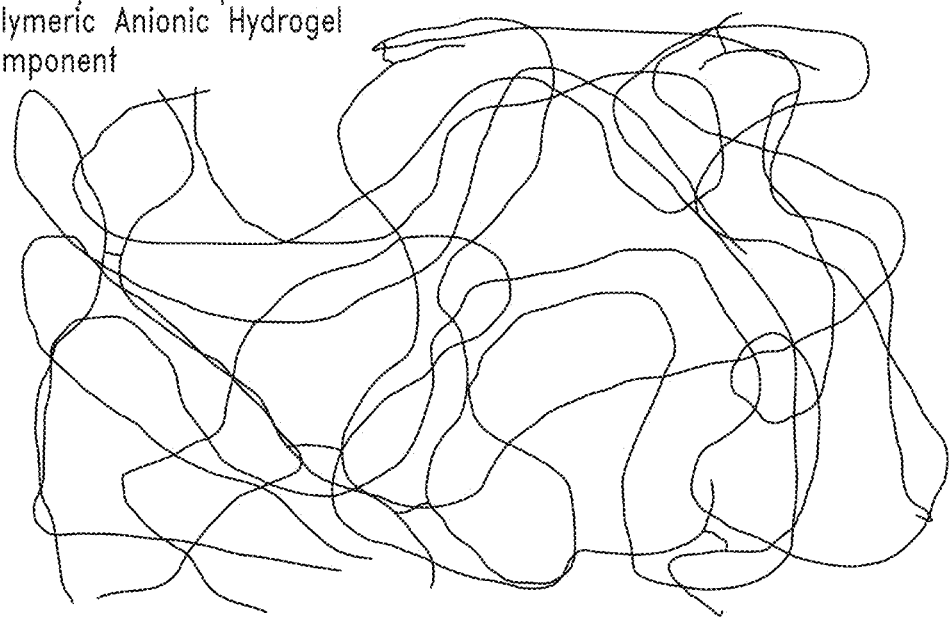
FIG. 3 shows a polymer/monomer solution after free radical polymerization of an anionic monomer.
Figure 4:
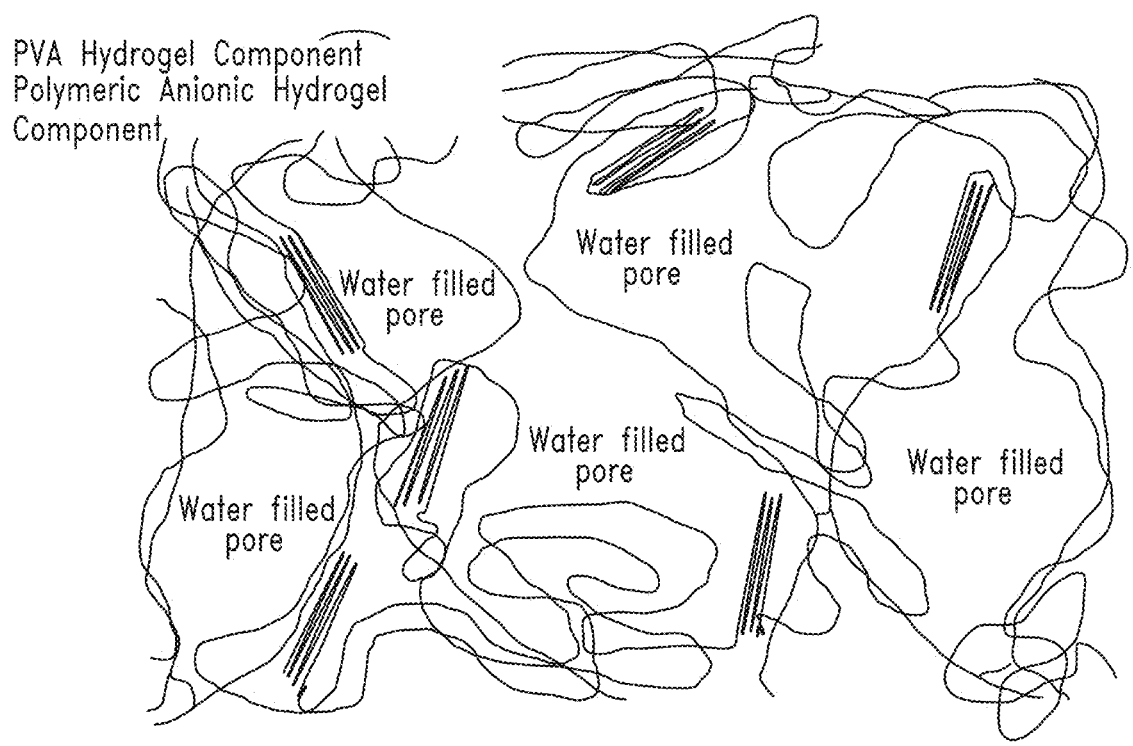
FIG. 4 shows a double network hydrogel system after freeze thaw cycles with PVA polymer and anionic hydrogel.
Figure 5:
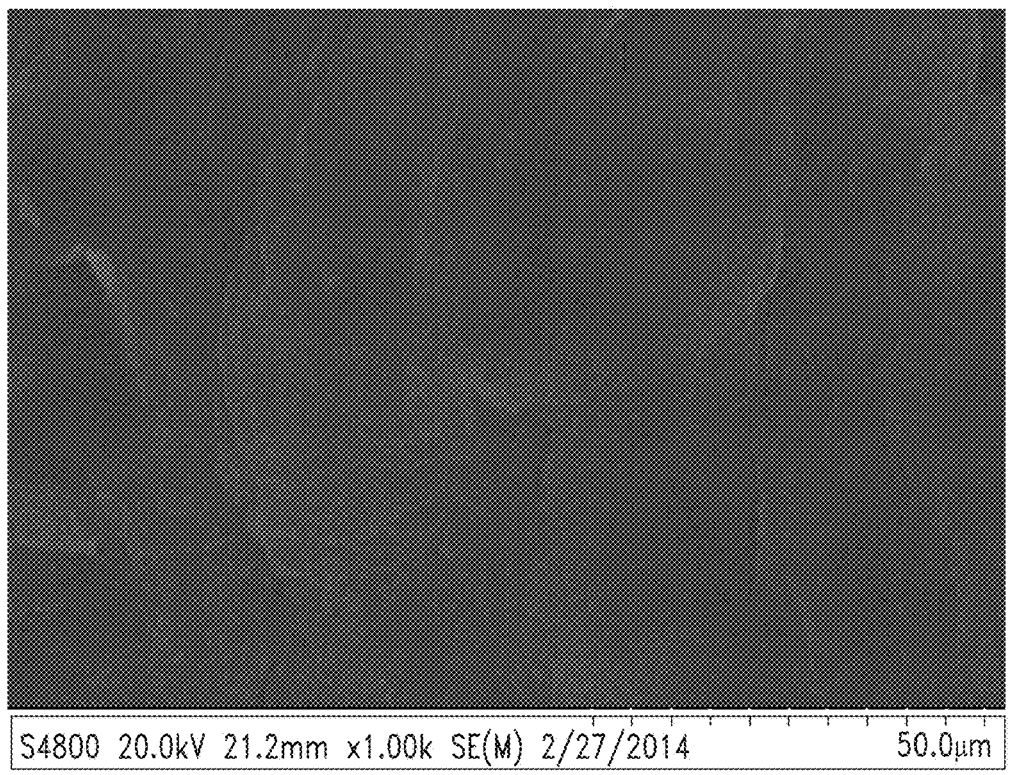
FIG. 5 shows a PVA Hydrogel Cross Section Post Freeze-drying.
Figure 6:
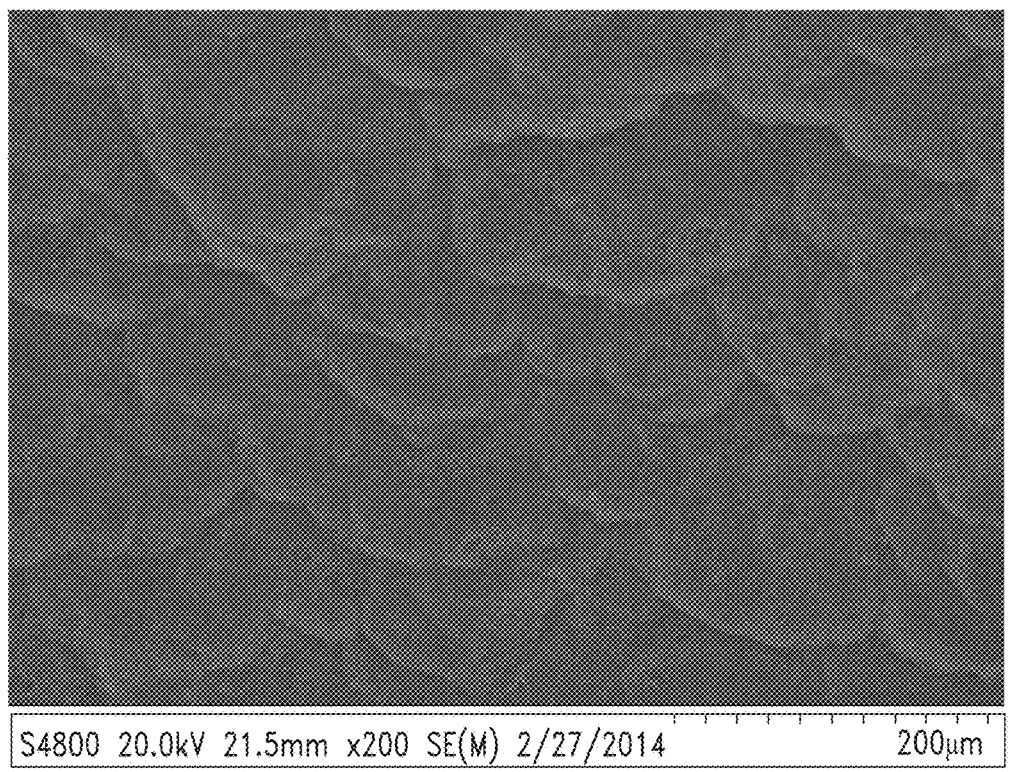
FIG. 6 shows a 90/10 PVA/PAA Hydrogel Cross Section Post Freeze-drying of the current disclosure showing pore preservation.

For illustrative purposes only, FIGS. 2-4 illustrates the formation of a double network hydrogel of one embodiment of the disclosure. FIG. 2 shows an initial polymer/monomer solution in water. FIG. 3 shows the polymer/monomer solution after free radical polymerization of an anionic monomer. FIG. 4 shows a double network hydrogel system after freeze thaw cycles with PVA polymer and anionic hydrogel. FIGS. 5 and 6 show electron microscopy images showing the preservation of pore structure in one embodiment of the disclosure. FIG. 5 shows a 30% PVA Hydrogel Cross Section Post Freeze-drying. FIG. 6 shows a 90/10 PVA/PAA Hydrogel Cross Section Post Freeze-drying of the current disclosure showing pore preservation (30% polymer solution). One major challenge in utilizing PVA physically cross-linked hydrogels for soft tissue replacement is mimicking both mechanical and tribological function. In order to increase the strength of the PVA hydrogels, the hydrogels are commonly dehydrated and annealed to increase the crystallinity. This procedure increases the mechanical strength (for example, modulus) however decreases the tribological properties (for example, coefficient of friction) due to pore collapse and reduction of equilibrium water content. Work done by Choi, suggests an extra step of PEG doping and rinsing to maintain pore size. Work by Muratoglu described the incorporation of free-radically polymerized polyacrylamide to maintain the pore size of physically cross-linked PVA hydrogels. Further work by Muratoglu improved upon the second network strategy by adding an ionic hydrogel into the physically cross-linked PVA. However, this work is not tailored to articular cartilage properties. In this embodiment, the compositions may be tailored to prevent pore collapse and maintain high equilibrium water content. This may allow for low coefficient of friction. In addition, the composition may be tailored to meet the specification of poison's ratio, Young's modulus, aggregate modulus, and hydraulic permeability. These specific compositions and methods allow for a material that will directly mimic the mechanical and tribological function of cartilage.

In a further embodiment, the synthetic soft tissue replacement of the current disclosure may be formed into an interpositional device, cartilage plug, and cap to replace damaged or worn cartilage. The device may be comprised of at least one other material to form the interpositional device, cartilage plug, and cap. Such interpositional devices are described by Fell et al., see U.S. Pat. Nos. 6,923,831, 6,911,044, 6,866,684, and 6,855,165 all of which are hereby incorporated herein by reference. The interpositional device could apply to toe, ankle, knee, intervertebral disc, wrist, finger, and shoulder applications. Such cartilage plugs are described by Simon et al., see U.S. Pat. Nos. 6,632,246 B1 and 6,626,945 B2 all of which are hereby incorporated herein by reference. The cartilage plugs could apply to toe, ankle, knee, hip, intervertebral disc, wrist, finger, elbow, and shoulder applications. Such caps are described by Frauens et al., see U.S. patent application Ser. Nos. 12/273,812 and 13/760,161, all of which are hereby incorporated herein by reference. The caps could apply to toe, ankle, knee, hip, intervertebral disc, wrist, finger, elbow, and shoulder applications. These devices can have a variety of shapes and sizes.

For a hydrogel inter positional device to perform in vivo in the long-term, the device desirably needs to have the mechanical and tribological properties outlined in this embodiment, such as for example, and not intended to be limiting, a high creep resistance. This is to minimize the changes to the shape of the interpositional hydrogel device during in vivo use. PVA-hydrogel materials of the present disclosure show increased stiffness and display increased creep resistance. The hydrogel inter positional device according to the present disclosure may also have superior mechanical properties, such as toughness, wear resistance, high creep resistance, high lubricity, cartilage-like ionic moieties, and the like.

In a preferred embodiment, a double network hydrogel is formed though a chemically cross-linked hydrogel and physically cross-linked PVA hydrogel wherein the chemically cross-linked hydrogel is synthesized from at least one anionic monomer and at least one non-ionic monomer. Each monomer is added directly (neat) to an aqueous PVA solution and agitated until a homogenous mixture of PVA polymer and monomer is achieved. A second aqueous based solution of initiator and cross-linker is added directly to the aqueous PVA and monomer solution. The resulting solution of PVA, initiator, cross-linker, and monomer are poured into a mold whereby the overall solution is reacted by either heat or UV to form a hydrogel with a semi-interpenetrating network (IPN). The semi-IPN can be converted into an IPN through at least one freeze-thaw cycle.

In another embodiment, the chemically cross-linked hydrogel of the double network hydrogel is synthesized from at least two anionic monomers, wherein each monomer has a different ionic strength at physiological conditions and at least one other non-ionic monomer or cationic monomer.

In another embodiment, the chemically cross-linked hydrogel of the double network hydrogel is synthesized from at least one anionic monomer and at least one non-ionic monomer bearing a minimum of one hydroxyl group.

In another embodiment, the chemically cross-linked hydrogel of the double network hydrogel is synthesized from at least one anionic monomer and at least one non-ionic monomer, wherein the non-ionic monomer may degrade over time resulting in an ionic repeat unit.

In another embodiment, the chemically cross-linked hydrogel of the double network hydrogel is synthesized from at least two non-ionic monomers, wherein at least one non-ionic monomer may degrade over time resulting in an ionic repeat unit.

In another embodiment, the hydroxyl group in the chemically cross-linked hydrogel may hydrogen bond with the aqueous PVA upon polymerization of the chemically cross-linked network. In addition, the chemically cross-linked hydrogel may crystalize with PVA.

In another embodiment, the IPN of physically cross-linked PVA and chemically cross-linked hydrogel may be converted to a single polymer network by chemically bonding the PVA network to the chemically cross-linked hydrogel network using a single chemical reaction or a combination of chemical reactions, i.e., a single reaction mechanism or a combination of reaction mechanisms can be used to chemically bond the two components of the network to form one continuous network. In another embodiment, the physically cross-linked PVA in the IPN may undergo chemical crosslinking between polymer chains of the PVA, but the IPN structure is maintained. In another embodiment, chemical crosslinking can be used to further modify the double network by chemically bonding/linking polymer chains of the PVA component, while still maintaining a double network system as opposed to forming a continuous network (the polymer chains of the first and second components are not chemically cross-linked to one another—the PVA component is cross-linked such that it ultimately is in the form of a physically and chemically crosslinked component of the two component network. This provides an additional form of the network such that, instead of having a physically cross-linked PVA component combined with chemically cross-linked the anionic component, there is additional chemical crosslinking used to modify the PVA component—which results in different mechanical properties such as increased Young's modulus and aggregate modulus compared to the DN without chemically crosslinked PVA. The chemical crosslinking of a minimum of one network may be reacted by either a water soluble aldehydes or irradiation. The chemical crosslinking of the PVA component can be accomplished by reacting with aldehydes, particularly water soluble aldehydes which include formaldehyde, glutaraldehyde, acetaldehyde, and succinaldehyde. Combinations of water soluble aldehydes can be used for crosslinking PVA, as this mechanism is not limited to the use of a single compound to crosslink PVA. A water soluble form of aldehyde is necessary to swell into the network at a lower temperature (less than 25° C.), and subsequently react at a higher temperature for homogenous chemical bonding throughout the hydrogel. The aqueous cross-linker concentration should be preferably less than 5%, more preferably less than 3%, and even more preferably less than 1%. After chemical crosslinking, the residual cross-linker and unreacted cross-linker can be quenched by the addition of an aqueous polyol (for example, glycerol, erythritol, dierythritol, xylitol, arabitol, mannitol, sorbitol). The aqueous polyol should be added at a concentration >1%, more preferably >3%, and even more preferably >5% with a preferred range of 3-6%. After quenching, the polymer network can be washed in deionized water or saline with a minimum of one rinse to remove reaction byproducts. The removal of residual polyol and aldehyde may be confirmed by IR, UV, GC, and HPLC. An alternative mechanism for crosslinking the PVA component involves the use of gamma or e-beam irradiation, such that carbon-carbon chemical bonds are formed between the backbone of the polymer chain. With this particular reaction mechanism, the backbone of the PVA and chemically crosslinked hydrogel may be bonded together through carbon-carbon chemical bonds. The irradiation dose must be conducted at 15-100 kGy and more preferably 15-30 kGy.

After dissolution, the temperature of the PVA solution is reduced to <39° C. and preferably <30° C. The anionic and non-ionic monomers are added directly (neat) to the aqueous PVA solution and are agitated until the solution is homogenous. A second aqueous solution with a cross-linker, initiator, and organic solvent is added to the aqueous PVA solution at a temperature <39° C. The PVA and monomer solution is poured directly into a mold with at least one surface that is UV transparent.

In another embodiment, the aqueous PVA solution will be physically cross-linked through freezing and thawing the solution for 1 cycle to form a physically cross-linked hydrogel. The anionic monomer within the physically cross-linked polymer may be polymerized by heat or irradiation to directly form an interpenetrating network. Additional, freeze thaw cycles may be performed to increase the crystallinity and modulate the porous structure of the PVA physically cross-linked component.

An additional embodiment of this disclosure is having a low freezing temperature <−20° C. and more preferably <−65° C., even more preferably <−75° C., and even more preferably <−80° C. during preparation of the DN hydrogel. The freezing rate of the water to ice transition should be >−0.001° C./min and more preferably <−0.1° C./min, even more preferably <−0.3° C./min, even more preferably <−0.5° C./min, and even more preferably <−5.0° C./min. The rate of temperature change of the mold surface for the freezing process should be <−1.0° C./min, more preferably <−10° C./min, even more preferably <−15° C./min, and even more preferably <−20° C./min. The thawing rate of the ice to water transitions should be <0.2° C./min, more preferably <0.1° C./min, and even more preferably <0.01° C./min.

An additional embodiment of this disclosure is selection of molding materials suitable for high temperature freezing. For highest freezing rates a molding material may be selected with a thermal conductivity >10 W/(m K) and more preferably >150 W/(m K), and even more preferably >200 W/(m K). The material with a high thermal conductivity will preferably have a thickness <1.5 in., more preferably <0.5 in., and even more preferably <0.25 in.

An additional embodiment of this disclosure is selection of molding materials suitable for high temperature freezing. For lower freezing rates a molding material may be selected with a thermal conductivity <1.5 W/(m K) and more preferably >1.0 W/(m K), and even more preferably >0.5 W/(m K). The material with a high thermal conductivity will preferably have a thickness <1.5 in., more preferably <0.5 in., and even more preferably <0.25 in.

An additional embodiment of this disclosure is selection of molding materials suitable for high temperature freezing. Molding materials may be selected from at least 2 different components with one component having a high thermal conductivity, and a second component having a low thermal conductivity (as described herein).

In additional embodiments, the present disclosure provides a double network hydrogel comprising two separate polymeric components, the first component comprising a chemically cross-linked anionic polymer and the second component comprising a physically cross-linked poly(vinyl alcohol). For instance, the present disclosure provides a double network hydrogel comprising a first network and a second network, where the first network is, or comprises, a first polymer, and the second network is, or comprises, a second polymer. The first polymer comprises —CH$_2$—CH(OH)— units, which may also be referred to as repeating units, which may be readily derived from polymerization of vinyl acetate followed by complete or partial hydrolysis of the acetate moieties. The first polymer may be a copolymer, made by, for example, copolymerizing vinyl acetate with one or more other monomers, and then hydrolyzing the acetate moieties to leave —CH$_2$—CH(OH)— units. Or the first polymer may be a homopolymer, prepared entirely from vinyl acetate followed by hydrolysis of some or all of the acetate moieties, which is referred to herein as polyvinylalcohol (PVA). The second network is, or comprises, a second polymer, where the second polymer comprises carboxyl (COOH)-containing units or salts thereof, sulfonyl (SO$_3$H)-containing units or salts thereof, and at least one of hydroxyl (OH)— containing units or amino (NH$_2$)-containing units. Thus the second polymer may also be identified as a terpolymer, since it will be made from at least three different monomers.

In exemplary embodiments, the DN hydrogels of the present disclosure may optionally be further described by any one or more (for example, two, three, four, five, six, etc.) of the options described herein, including the following. The first polymer is polyvinyl alcohol, which may have some residual amount of acetylation, typically less than 10 mol %. The first polymer may be a copolymer that includes —CH$_2$—CH(OH)— units, where the copolymer will include units other than —CH$_2$—CH(OH)— units, e.g., units derived from other vinyl monomers. The carboxyl-containing units which are present in the second polymer may be derived from a monomer selected from acrylic acid (AA) and methacrylic acid (MA). In one embodiment, the carboxyl-containing units are derived from acrylic acid. The sulfonyl-containing units which are present in the second polymer may be derived from a monomer selected from 3-sulfopropyl methacrylate, 3-sulfopropyl acrylate, 2-sulfoethyl methacrylate, 2-propene-1-sulfonic acid, and 2-acrylamido-2-methylpropane sulfonic acid (AMPS). In one embodiment, the sulfonyl-containing units are derived from AMPS. The second polymer contains amino-containing units, where those amino-containing units may be derived from acrylamide (AAm). The second polymer contains hydroxyl-containing units, where those hydroxyl-containing units are derived from a monomer selected from N-(tris (hydroxymethyl)methyl)acrylamide and N-hydroxyethyl acrylamide. Thus, for example, the first polymer may be polyvinyl alcohol and the second polymer may be formed from monomers including each of AA, AMPS and AAm, plus an optional crosslinking agent if a chemically crosslinked second polymer is desired. Optionally, the first polymer may be a polyvinyl alcohol and the second polymer may be formed from monomers consisting of, or consisting essentially of, AA, AMPS and AAm, plus an optional crosslinking agent if a chemically crosslinked second polymer is desired. The first polymer is made from x moles of monomer(s) and the second polymer is made from y moles of monomer(s), and x/(x+y) is at least 0.7, or at least 0.75, or at least 0.8, or at least 0.85, or at least 0.9, or at least 0.95. For example, the DN hydrogel may be prepared from a specified weight of PVA having a known molecular weight, which provides x moles of the monomer(s) used to prepare the PVA, and the specified weight of PVA is added to a reaction vessel with y moles of monomers used to prepare the second polymer, and x/(x+y) is at least 0.7, or at least 0.75, or at least 0.8, or at least 0.85, or at least 0.9, or at least 0.95. The term monomer(s) refers to one or more different monomers. The first network may be semi-interpenetrated with the second network. The first network may be physically crosslinked, e.g., by one or more freeze thaw cycling as described herein. The second network may be chemically crosslinked, e.g., by including a crosslinking agent among the monomers that are used to prepare the second polymer, where N,N'-methylenebisacrylamide (MBAA) is an exemplary crosslinker. Thus, the second polymer may comprise crosslinking units derived from a crosslinking agent, where the crosslinking agent provides not more than 2.5 molar units, based on a calculation where (a) the carboxyl (COOH)-containing units or salts thereof, (b) the sulfonyl ($SO_3H$)-containing units or salts thereof, (c) the at least one of hydroxyl (OH)-containing units or amino ($NH_2$)-containing units, and (d) the crosslinking units provide a total of 100 molar units. In a preferred embodiment, the hydrogel is in the form of a hybrid double network hydrogel wherein the first network is physically crosslinked and the second network is chemically crosslinked.

In another embodiment the present disclosure provides a composition that comprises a DN hydrogel as described herein, and water, which may be referred to as an aqueous composition. Optionally, the water includes dissolved salt(s) to provide saline, i.e., a combination of water and salt, where the salt may be, or include, sodium chloride. Optionally, the water includes dissolved buffering agents, e.g., buffering agents to provide aqueous PBS buffer, where the buffer optionally provides a pH for the composition in the physiological range for placing the composition into an animal's joint. Optionally, the aqueous composition is sterile. Optionally, the aqueous composition exhibits a poroelastic response.

In another embodiment, the present disclosure provides a polymer that may be used to prepare a DN hydrogel of the present disclosure. For example, the present disclosure provides a polymer prepared from the monomers acrylic acid (AA), acrylamide (AAm), 2-acrylamido-2-methylpropane sulfonic acid (AMPS) and a crosslinking agent. Optionally, the monomers constitute 50-75 wt % AA, 10-35 wt % AMPS and 5-25 wt % AAm, the sum of the monomer weight percentages equaling 100. Optionally, the crosslinking agent is N,N'-methylenebisacrylamide (MBAA).

FIG. 7 shows formulations of PVA Double Network Hydrogels. FIG. 8, meanwhile, shows properties of PVA Double Network Hydrogels. The mechanical properties of the PVA double network hydrogels indicate that the incorporation of the chemically cross-linked hydrogels with an ionic and non-ionic component results in an increase in Young's modulus over PVA hydrogel controls. In addition, the increase in mechanical strength is achieved with a greater water volume fraction. Typically, PVA hydrogels decrease in mechanical strength with increasing water volume fraction. The modulation in the amount of the chemically cross-linked network significantly affects the water volume fraction of the hydrogels.

Prior work, such as U.S. Pat. Pub. No. 2011/0054622, focuses on contacting an aqueous solution of a polymer with an aqueous solution of an ionic monomeric or polymeric compound in presence of an initiator, thereby forming an ionic hydrogel solution. Making an aqueous solution of the monomer with the initiator prior to mixing with PVA will result in a partially cured or pre-gelled mixture of a hydrogel. In one embodiment, the method described in this disclosure adds a monomer component directly (neat) into a PVA solution and is mixed to form a homogenous mixture. Once the homogenous aqueous solution of PVA and monomer (ionic and non-ionic monomer) are mixed, the aqueous based solution of the initiator and cross-linker are added to the system. This method allows for all potential reactions to occur once the overall double network hydrogel solution is thoroughly mixed.

In further embodiments, structural modulation of PVA hydrogels through physical and chemical crosslinking, and methods therefore, are disclosed. In one embodiment, a method to modify the macrostructure of polyvinyl alcohol (PVA) hydrogels through physical crosslinking is provided. Physically cross-linked hydrogels may be additionally cross-linked by one or more chemical bonding mechanisms. In this invention, the macrostructure of PVA hydrogels is modulated through physical crosslinking, and additional chemical crosslinking may be used to fix the amorphous regions of a PVA hydrogel after physical crosslinking. Specifically, the morphology in PVA hydrogels is modified to reduce pore diameter to submicron (<1 micron) pores.

PVA hydrogels have many promising properties, such as high water content, high mechanical strength, porous structure, and excellent biocompatibility that make them great candidates for an array of biomedical applications. Unlike most chemically cross-linked hydrogels, physically cross-linked PVA hydrogels include three separate regions: 1) crystalline regions; 2) hydrated amorphous regions; and 3) water porous regions. (Gonzalez, J. S., & Alvarez, V. A. (2011). The effect of the annealing on the poly(vinyl alcohol) obtained by freezing-thawing. Thermochimica Acta, 521(1-2), 184-190.). Prior uses have commonly focused on methods to modulate the crystalline structure of PVA hydrogels (Gonzalez & Alvarez, 2011; Hassan, C. M., & Peppas, N. A. (2000) Structure and Morphology of Freeze/Thawed PVA Hydrogels, Macromolecules, 33(7), 2472-2479). More recent researchers have begun to investigate the macrostructure of PVA hydrogels through directional freeze thawing between two plates (Zhang, L., Zhao, J., Zhu, J., He, C., & Wang, H. (2012). Anisotropic tough poly(vinyl alcohol) hydrogels, Soft Matter, 8, 10439). However, these references are silent on how to reduce pore diameter, modulate pore shape, and increase the number of pores. This disclosure describes a method to decrease pore diameter, modulate pore shape, and increase the number of pores. In addition, the disclosure includes modulating the macrostructure of the mechanical properties and mechanical mechanisms of PVA hydrogels.

With respect to synthesis of PVA hydrogels, data is lacking regarding the specific description for the freezing rate for PVA hydrogels. Typically, the freezing rate of physically cross-linked PVA hydrogels has been described by freezing temperatures (Hassan & Peppas, 2000; Ricciardi et al., 2005; Wang & Campbell, 2009) and overall freezing rate (Wang & Campbell, 2009). In addition, data has not been provided to describe all of the factors that affect the heat transfer such as mold material, mold thickness, volume of aqueous PVA, molecular weight of PVA, crystallinity of PVA, concentration of PVA, and convection/conduction.

Figure 9A:
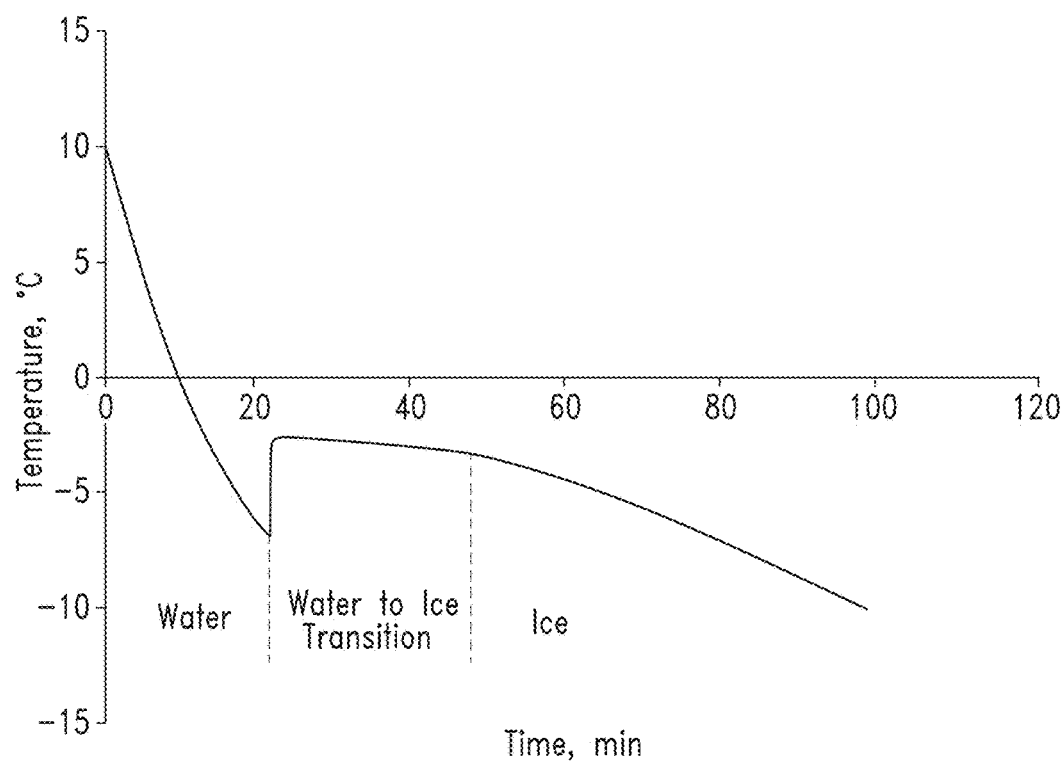
FIGS. 9A and B show typical temperature versus time of freezing and thawing cycles for 30 weight percent PVA hydrogels frozen at −20° C.
Figure 9B:
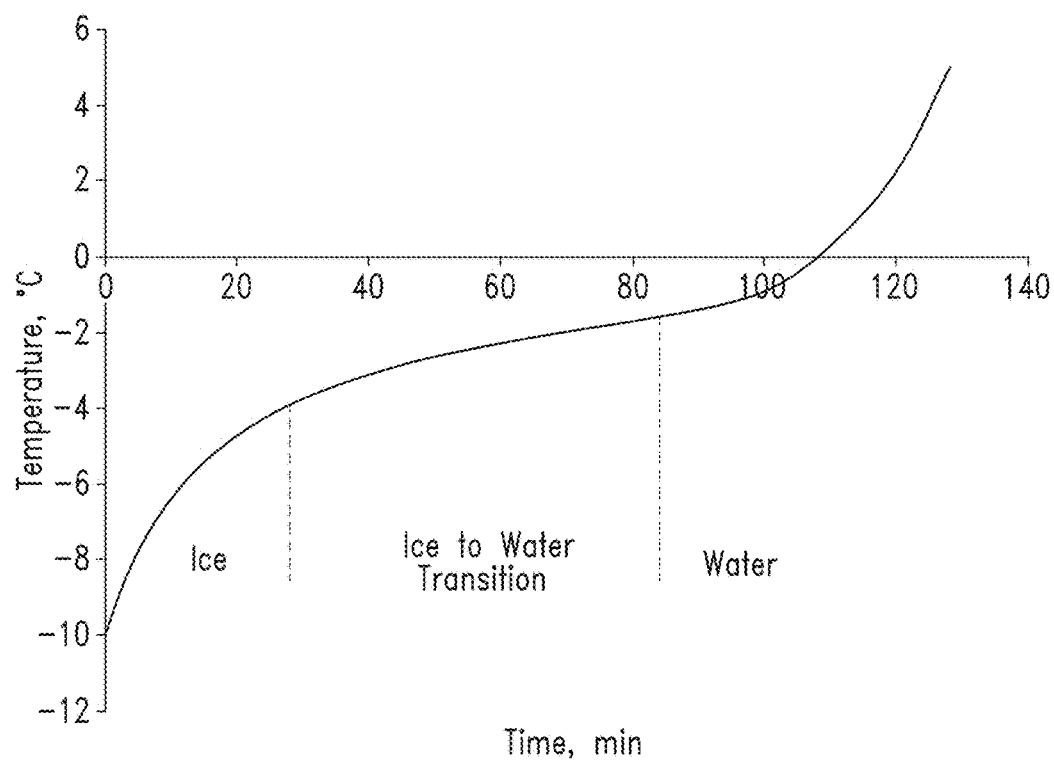
(FIG. 9B).

The current disclosure describes the freezing rate of PVA by directly measuring the temperature change occurring in an aqueous PVA solution and determining the rate of the ice to water and water to ice transitions, see FIG. 9. FIG. 9 shows typical temperature versus time response of freezing and thawing cycles for 30 wt. % PVA hydrogels frozen at −20° C. and thawed at 20° C. Panel a of FIG. 9 shows the freezing cycle and panel b shows the thawing cycle. With a more precise measurement of freezing rate, the current disclosure shows that high freezing rates decrease pore diameter and increase pore distribution/number of pores. Additional changes in the macrostructure of PVA hydrogels may be made by modulating the concentration of aqueous PVA and the number of freeze thaw cycles.

Physically and chemically cross-linked PVA hydrogels were synthesized with PVA having a minimum degree of polymerization of 2200, which is determine from the molecular weight measured by GPC. PVA may have a degree of hydrolysis >85%, more preferably >90%, and even more preferably >98%, which is determined by a hydrolysis of the PVA followed by titration. Aqueous solutions of PVA can be made with deionized water or saline solutions. These solutions may have a range of 10-40% PVA, more preferably 15-35% PVA, and even more preferably from 15-30% PVA. The solutions of PVA are measured gravimetrically by weighing out on a balance.

An additional aspect of this disclosure is directed to controlling/engineering pore connectivity and pore distribution by increasing the number of freeze thaw cycles between 1 and 10 cycles with the majority of macrostructure changes happening between 1 and 6 cycles. Although 10 and 6 cycles are disclosed herein, more or less cycles are considered within the scope of this disclosure in order to craft PVAs with desired properties.

Moreover, decreasing the concentration of PVA will also help control/engineer the resulting pores. For purposes of example only and not intended to be limiting, reducing the PVA concentration from 40% to 10%, may affect the number of pores, pore connectivity, pore shape, and pore distribution/density. Highly porous networks of PVA may be synthesized by concentrations preferably <20% PVA, and more preferably <15% PVA. Porosity may be decreased by increasing the PVA concentration preferably >20%, more preferably >30%, and even more preferably >35%.

An additional embodiment provides a method of freezing PVA hydrogels or double network hydrogels at a low freezing temperature such as <−61° C. and more preferably <−75° C., and even more preferably <−80° C. The freezing rate of the water to ice transition should be <−0.1° C./min and more preferably <−0.3° C./min, even more preferably <−0.5° C./min, even more preferably <−1° C./min. The rate of temperature change of the mold surface for the freezing process should be <−5.0° C./min, more preferably <−10° C./min, even more preferably <−15° C./min, and even more preferably <−20° C./min. The thawing rate of the ice to water transitions should be <0.2° C./min, more preferably <0.1° C./min, and even more preferably <0.01° C./min.

In a further embodiment of this disclosure, the method includes selection of molding materials at high temperature freezing. For highest freezing rates a molding material may be selected with a thermal conductivity >10 W/(m K) and more preferably >150 W/(m K), and even more preferably >200 W/(m K). The material with a high thermal conductivity will preferably have a thickness <1.5 in., more preferably <0.5 in., and even more preferably <0.25 in. Some suitable materials include stainless steel, aluminum, copper, nickel, silver, and combinations thereof.

In an alternative embodiment, for lower freezing rates a molding material may be selected with a thermal conductivity <1.5 W/(m K) and more preferably >1.0 W/(m K), and even more preferably >0.5 W/(m K). The material with a high thermal conductivity will preferably have a thickness <1.5 in., more preferably <0.5 in., and even more preferably <0.25 in. Some suitable materials include glass, polystyrene, polycarbonate, polymethyl methacrylate, polypropylene, polyethylene, polytetrafluoroethylene, polyether ether ketone, and combinations thereof.

An additional embodiment of this disclosure includes selection of molding materials suitable for high temperature freezing. Molding materials may be selected from at least 2 different components with one component having a high thermal conductivity, and a second component having a low thermal conductivity (as described herein). The high thermal conductivity material may comprise of stainless steel, aluminum, copper, nickel, silver, and combinations thereof. The low thermal conductivity material may comprise of glass, polystyrene, polycarbonate, polymethyl methacrylate, polypropylene, polyethylene, polytetrafluoroethylene, polyether ether ketone, and combinations thereof.

When synthesizing highly porous PVA hydrogels, there is commonly a tradeoff between porosity and mechanical strength (for example, Young's modulus). Typically, hydrogels are dehydrated and annealed to increase the PVA crystallinity therefore improving the mechanical properties. However, this approach results in pore collapse and decrease in water content. The method described herein provides a way to improve the strength of PVA physically cross-linked hydrogels and minimize the pore collapse and reduction in water content. The reduction in mechanical strength is believed to be a result of water plasticizing the amorphous phase, and therefore use of a crosslinking agent to chemically bond the amorphous phase of the PVA hydrogel may be employed.

Prior to chemical crosslinking, the PVA hydrogel preferably has a minimum of one freeze thaw cycle with a crystalline domain. The number of freeze/thaw cycles will preferably be >3, more preferably >5, and even more preferably >8. The crosslinking agent may be selected from a group of water soluble aldehydes (for example, formaldehyde, glutaraldehyde, acetaldehyde, succinaldehyde). The cross-linker may be added to swell into the network at a lower temperature (such as less than 25° C.), and subsequently reacted at a higher temperature for homogenous chemical bonding throughout the hydrogel. The aqueous cross-linker concentration should be preferably less than 5%, more preferably less than 3%, and even more preferably less than 1%. After chemical crosslinking, the residual cross-linker and un-reacted cross-linker may be quenched by the addition of an aqueous polyol (for example, glycerol, erythritol, dierythritol, xylitol, arabitol, mannitol, sorbitol). The aqueous polyol should be added at a concentration >1%, more preferably >3%, and even more preferably >5% with a preferred range of 3-6%. After quenching, the polymer network can be washed in deionized water with a minimum of one rinse to remove reaction byproducts. The removal of residual polyol and aldehyde may be confirmed by UV, GC, and HPLC.

A particularly preferred aspect of a physical and chemical cross-linked PVA is an increase in Young's modulus by >3% more preferably >10%, and even more preferably >15% in relation to the physically cross-linked PVA hydrogel of the same concentration. In addition, the physical/chemical cross-linked hydrogel may have a further reduction in pore size by >2%, preferably >5%, and even more preferably >7%.

In another embodiment, the physically cross-linked hydrogel has a minimum of 1 freeze thaw cycle and a crystalline domain. The number of freeze/thaw cycles will preferably be >3, more preferably >5, and even more preferably >8. The physically cross-linked hydrogel may undergo chemical cross-linking by a minimum of two different chemical bonding mechanisms. The first chemical crosslinking will be conducted as described herein. The second chemical crosslinking will be conducted by gamma or e-beam irradiation. The irradiation dose must be conducted at 15-100 kGy and more preferably 15-30 kGy.

A particularly preferred aspect of a physical and twice chemically cross-linked PVA is an increase in Young's modulus by >3%, more preferably >10%, and even more preferably >15% in relation to the physically cross-linked PVA hydrogel of the same concentration. In addition, the physical and twice chemically cross-linked hydrogel may have a further reduction in pore size by >2%, preferably >5%, and even more preferably >7%.

Figure 10:
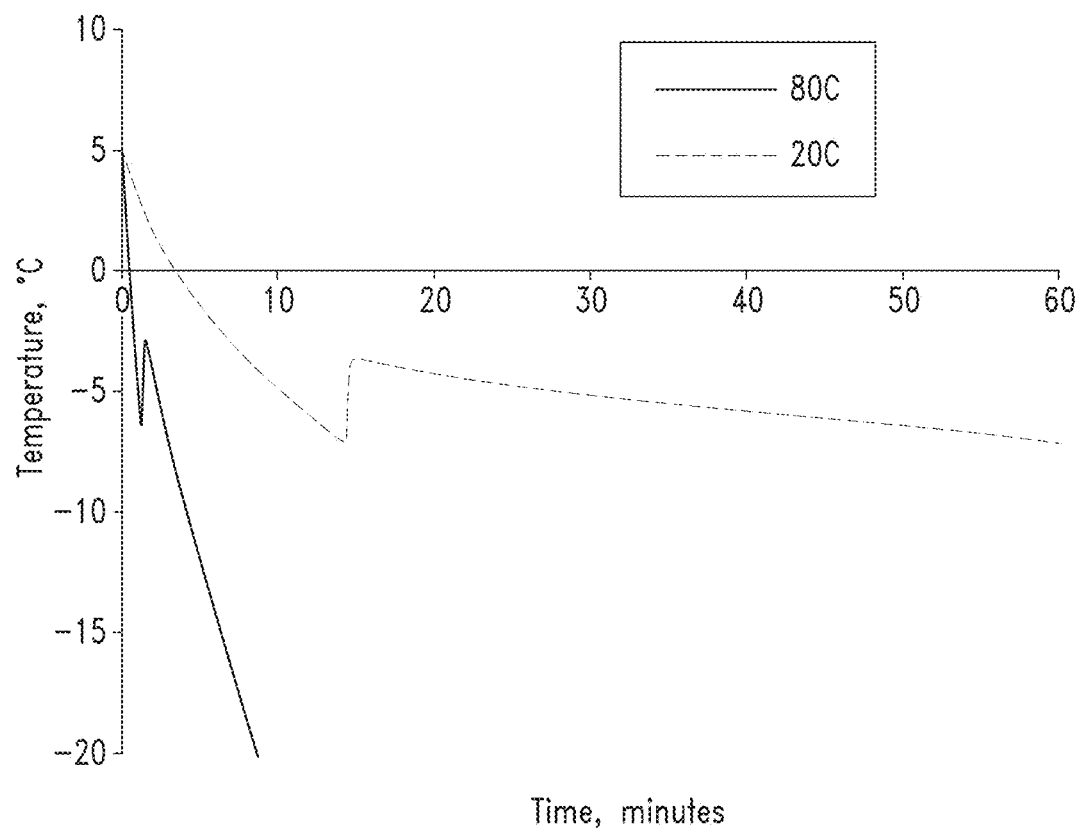
FIG. 10 shows typical temperature versus time response of a freezing cycle for 30 wt. % PVA hydrogels frozen at −20° C./7.89×10$^{-2}$° C./min and −80° C./2.73° C./min.
Figure 11A:
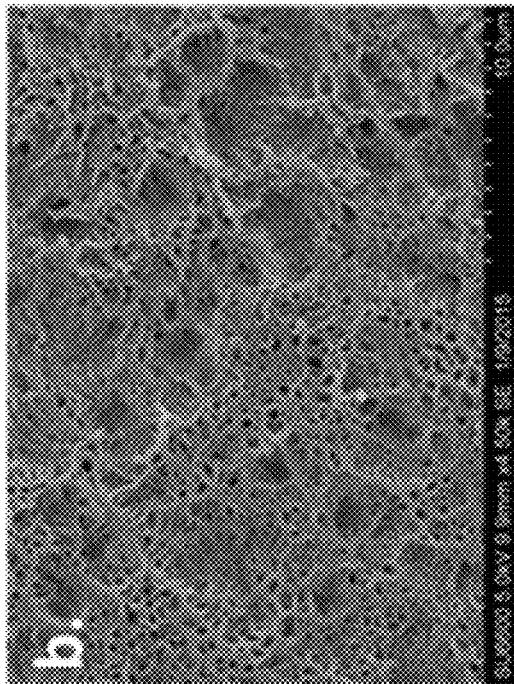
FIG. 11A-D show the morphology of a 30% PVA (Mn≈145,000, 99% Hydrolyzed) hydrogel with 9 freeze cycles at −20° C. and 9 thaw cycles at room temperature.
Figure 11B:
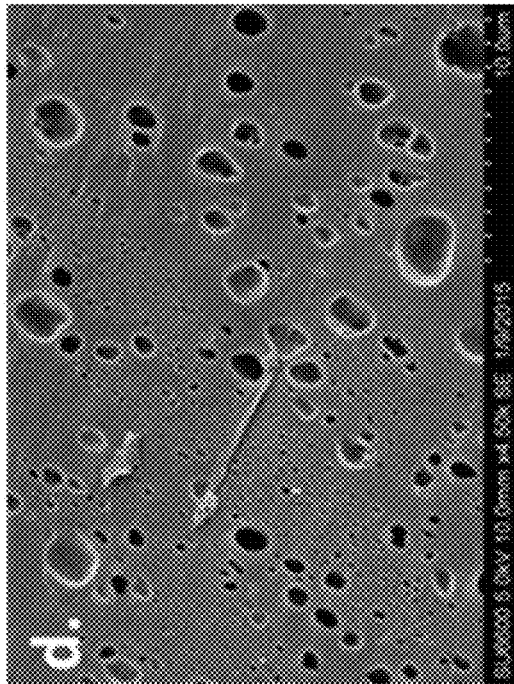
Figure 11C:
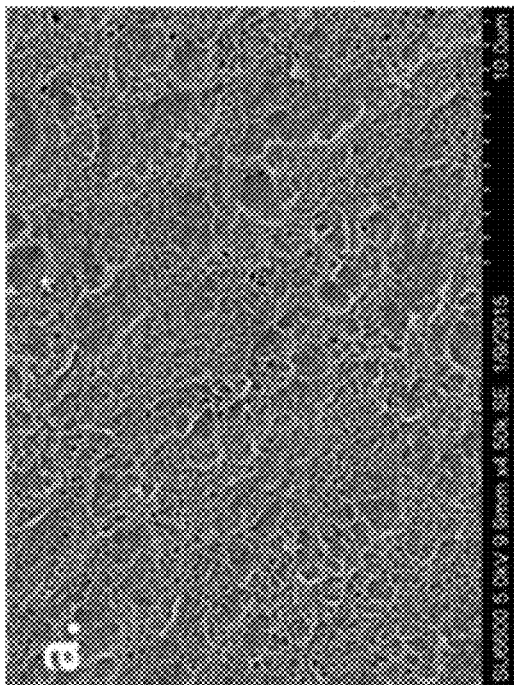
Figure 11D:
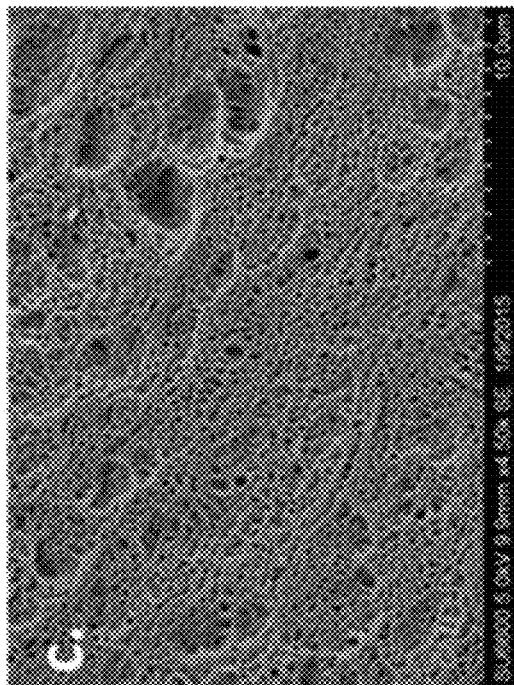

Typically, the freeze/thaw conditions for synthesis of physically cross-linked PVA hydrogels is reported in freezing and thawing temperature. However, it has been discovered that the process of synthesizing PVA hydrogels is a rate dependent process of ice and polymer crystallization during subsequent freezing and thawing cycles. One focus of the current disclosure is to standardize these values by reporting not only the temperature but the rate of the freeze/thaw cycles. FIG. 10 shows a typical freezing and thawing cycle illustrated at −20° C. The important slope of the curve to determine the freezing/thawing rate occurs between the transitions from the water to ice/ice to water state as displayed in FIG. 11. FIG. 11 shows the morphology of a 30% PVA (Mn≈145,000, 99% Hydrolyzed) hydrogel with 9 freeze cycles at −20° C. and 9 thaw cycles at room temperature viewed via scanning electron microscopy (SEM). The images were taken from the following perspectives of cylindrical molded PVA hydrogels: a) bottom, b) top, c) side, and d) cross-section. In preliminary studies, the freezing rate was increased through decreasing the temperature of freezing from −20° C. to −80° C. In response, PVA hydrogels that were frozen at −80° C. in a polystyrene mold had a rate of 2.73° C./min, and samples frozen at −20° C. in the same mold material had a rate of $7.89 \times 10^{-2\circ}$ C./min.

In one example of the current disclosure, after hydrogels were synthesized at different freezing rates, the porous structure was evaluated for 30% PVA (Mn≈145 kDa, 99% hydrolyzed, 9 freeze/thaw cycles) hydrogels by SEM.

Figure 12B:
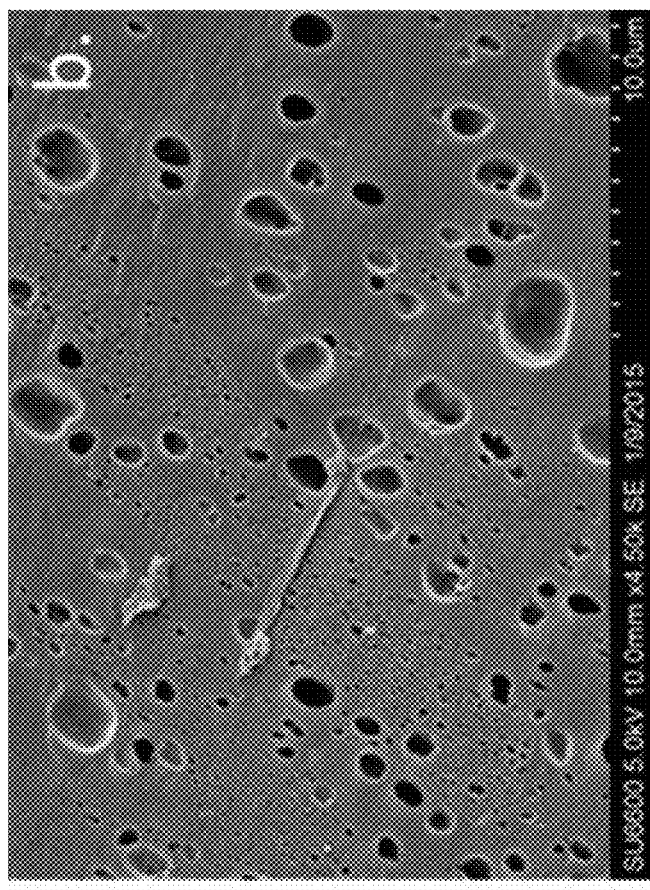
FIG. 12A-D show the effect of freezing rate on pore size and distribution (% Area) of 30 wt. % PVA Hydrogels (Mn≈145,000, 99% Hydrolyzed)
Figure 12A:
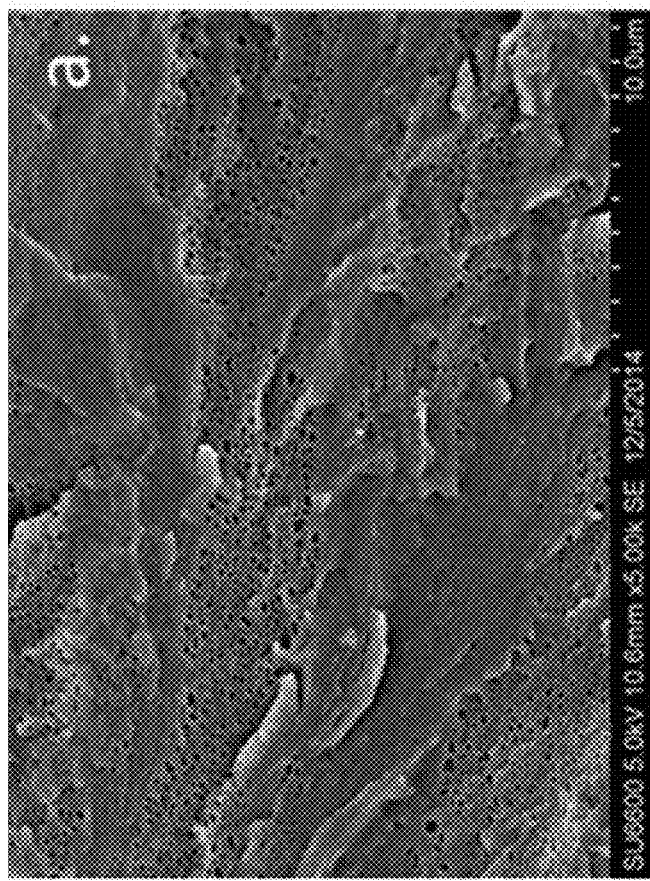
Figures 12C, 12D:
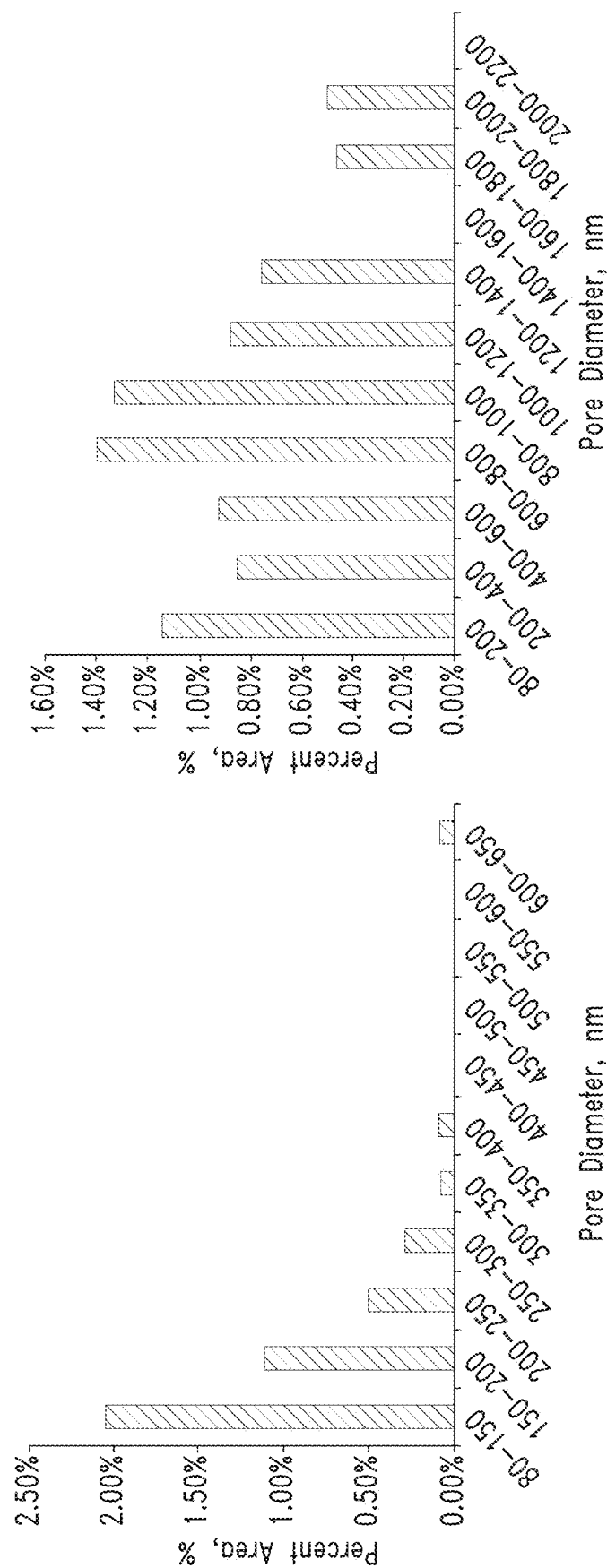

With respect to FIG. 11, the SEM images of the PVA hydrogels show the morphology of molded cylindrical disk from each side and the cross-section of the PVA hydrogel. The molded disks were formulated by the method as described herein with freezing at −20° C. and thawing at 20° C. From evaluating the outer surfaces, the PVA hydrogel appears to be highly porous with submicron pores. However, the cross-sectional image illustrates a network of pores ranging from 80 nm to 2.2 μm, see FIG. 12. FIG. 12 shows the effect of freezing rate on the pore size and distribution (% Area) of 30 wt. % PVA Hydrogels (Mn≈145,000, 99% Hydrolyzed): a) image with −80° C. freezing; 2.73° C./min freezing rate; b) image with −20° C. freezing temperature; $7.89 \times 10^{-2\circ}$ C./min freezing rate; c) pore size distribution at −80° C. freezing; and d) pore size distribution at −20° C. freezing. Additionally, PVA hydrogels were synthesized by freezing at −80° C. and thawing at 20° C. In FIG. 12, the pore size and distribution has drastically changed by varying the freezing rate from 2.73° C./min to 7.89×10-2° C./min. In the −80° C. freeze cross-sectional image, there are no pores that are greater than one micron. In addition, the pores are more evenly distributed over the region of interest.

FIG. 13 shows a table illustrating the effect of effect of freeze rate and concentration on the mechanical properties of PVA Hydrogels of the current disclosure.

FIG. 14 shows a table illustrating the effect of freeze rate and concentration on the water volume fraction and percent crystallinity of PVA hydrogels of the current disclosure. FIG. 14 illustrates that both concentration and freezing temperature/rate do not have a significant difference in the crystallinity of the dry PVA hydrogel. However, the concentration and freezing temperature/rate affects the overall water volume fraction of the hydrogel.

Over 700,000 total knee replacements (TKR) are performed each year in the United States with nearly half of these operations conducted on patients between 45 to 65 years old. Under the age of 40, the standard of care for repairing cartilage lesions is microfracture. However, this treatment is less effective in patients over 40 and especially ineffective in arthritic joints. Patients over 40 years old with joint pain are left with palliative treatment options until the eventual arthroplasty procedure. Because of this, many patients continue to live with joint pain trying to delay arthroplasty procedures until later in life. New treatment options are therefore needed to address the cause of pain due to cartilage lesions. One such approach would be to resurface the damaged cartilage tissue with a synthetic cartilage material without a total joint replacement. In one embodiment, the present disclosure provides a double network hydrogel and compositions thereof that may be used for this purpose. It is particularly desirable that the hydrogel mimic the mechanical, tribological, and morphological properties of cartilage.

Accordingly, in one embodiment the present disclosure provides a method of improving an animal joint where the joint contains cartilage, the method comprising placing a double network hydrogel of the present disclosure in the joint to provide a synthetic cartilage for the joint. The method may include, for example, resurfacing the existing cartilage that lies within a joint with a layer of the double network hydrogel of the present disclosure. The method may include, for example, attachment of the hydrogel network material to the subchondral bone surface. Optionally, the hydrogel may be free floating in the joint space.

The animal that receives the DN hydrogel may be a human in need thereof. Alternatively, the animal may be any other animal with a joint problem that may benefit from receiving artificial cartilage, e.g., a horse, donkey, mule, cow, pig, dog, cat or monkey. For example, the animal may have arthritis, e.g., osteoarthritis. The DN hydrogel may be prepared to have a desired size, as tailored to the size and needs of the animal and the objectives of the attending physician who will implant the DN hydrogel into the subject.

In one embodiment, the present disclosure provides double network hydrogels capable of a poroelastic response wherein the loading mechanisms are similar to what is observed in native cartilage tissue. Towards achieving this objective, the present inventor discovered that the compressive modulus of DN hydrogels has an inverse relationship to the water content of the hydrogels. Over a range of porous structures, the conditions for a poroelastic response were found in 15% and 20% PVA hydrogels as observed through stress relaxation testing. The resulting poroelastic PVA hydrogels were then capable of reduced relative coefficient of friction in comparison to, e.g., 30% PVA hydrogels where a poroelastic response was not dominant.

Double network hydrogels consisting of a chemically crosslinked tunable anionic hydrogel and physically cross-linked PVA provide improvements in structural stability and compressive modulus as compared to PVA-only hydrogels. Specifically, the DN hydrogel can mimic the glycosaminoglycan's functionality in cartilage. The incorporation of the anionic hydrogel component, i.e., the first network of the double network hydrogel of the present disclosure, provided increased compressive modulus with respect to PVA-only hydrogels of comparable water content. DN hydrogels of the present disclosure therefore afford improved stiffness compared to PVA-only hydrogels with less compromise by loss of water content.

The porous structure of the DN hydrogels provided pore variability, sometimes resulting in large regions where no pores were present. This observation may be a consequence of the decreased crystallinity and greater swelling for DN hydrogels compared to PVA-only hydrogels.

The DN hydrogels were evaluated for in vitro cytotoxicity and in vivo tissue response. The in vitro cytotoxicity of the DN hydrogels was comparable to ultra-high molecular weight polyethylene (UHMWPE). The in vivo tissue response was evaluated at acute and subacute time points through the subcutaneous implantation in Sprague-Dawley rats. The DN hydrogel implants were well tolerated and comparable to the PVA-only hydrogel and UHMWPE control groups.

Thus, the present disclosure provides DN hydrogels exhibiting a poroelastic response and desirable performance properties as measured by compressive modulus. The DN hydrogels also exhibit good in vitro cytotoxicity and good in vivo tissue response, thus making them useful as cartilage replacement or cartilage supplement in a joint.

In order to attach the DN network hydrogel artificial cartilage to subchondral bone, an osteochondral plug consisting of a PVA hydrogel as a synthetic cartilage and titanium fiber mesh (TFM) as a porous artificial bone may be employed, as described in the art. See, e.g., Oka, M., et al., Clin. Mater. 1990, 6, 361-381; Oka, M., et al., Proc. Inst. Mech. Eng. Part H—Journal Eng. Med. 2000, 214, 59-68; Oka, M. Biomechanics and repair of articular cartilage, Orthop. Sci. 2001, 6 (5), 448-456; and Ushio, K., et al., J. Biomed. Mater. Res. B. Appl. Biomater. 2004, 68 (1), 59-68.

According to the present disclosure, novel double network hydrogel formulations were synthesized by first creating a semi-IPN by the photopolymerization of a tunable anionic hydrogel. Afterwards, trapped PVA in the anionic hydrogel was physically cross-linked through freeze thaw cycles which imparted crystallization of the PVA. The chemically cross-linked anionic hydrogel inhibited crystallinity of the PVA. Specifically, the anionic hydrogel compositions with increasing anionic hydrogel concentration, cross-linker concentration, and molar mass of monomer reduced the crystallinity of PVA especially after dehydration and rehydration of the double network hydrogels. With the reduction in crystallinity, the incorporation of the anionic hydrogel resulted in an increase in water content with values ranging from 73.8% to 87.5%. In general, an increased water content of PVA hydrogels results in decreases in the compressive elastic modulus. The incorporation of the anionic hydrogel for purposes of mimicking GAG functionality served to increase the stiffness of the PVA double network hydrogel formulations. This effect was illustrated through the increases in the compressive elastic modulus in comparison to PVA hydrogel controls of comparable water content. The double network hydrogel formulations had a compressive elastic modulus ranging from 0.317 MPa to 0.986 MPa which was dependent on the formulation and hydration conditions. For comparison, the typical Young's modulus for articular cartilage ranges from 0.45-0.80 MPa. In addition to compressive modulus, all PVA double network hydrogel formulations had increased free swelling diffusion coefficient and overall water content. Thus, PVA double network hydrogels can be synthesized to both increase water content and improve the compressive elastic modulus by the incorporation of a tunable anionic hydrogel into PVA hydrogels.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and Applicants reserve the right to revise the application or claims to refer specifically to any individual member or any subgroup of members of the Markush group.

The following Example is offered by way of illustration and not by way of limitation.

EXAMPLE

Polyvinyl alcohol (Miowol® 28-99) with a number average molecular weight of 145 kDa and a 99% degree of hydrolysis was purchased from Sigma-Aldrich. Additionally, acrylic acid (AA), acrylamide (AAm), N,N'-methylenebisacrylamide (MBAA), and 2-acrylamido-2-methylpropane sulfonic acid (AMPS) were obtained from Sigma-Aldrich. Irgacure® 2959 was acquired from Ciba, Inc.

Double network hydrogels were synthesized similar to previously cited methods (see, e.g., Choi, J. et al., J. Biomed. Mater. Res. B. Appl. Biomater. 2011, 524-532). According to the present disclosure, PVA was dissolved in deionized water at a 20 w/w % solution by heating to 95° C. until the solution was homogenous. The temperature was reduced to 30° C., and depending on the desired final composition, the AA, AAm and AMPS monomers were added neatly into the aqueous PVA solution. The monomers were mixed until the solution was homogenous by visual inspection. Finally, the photo-initiator (Irgacure® 2959) and cross-linker (MBAA) were dissolved in the mixture. The final solution was poured into an ultraviolet (UV) transparent mold to create cylindrical samples with a diameter of 16 mm and minimum height of 17 mm. The solution was photo-polymerized using a Blak-Ray® UV lamp at 365 nm. After chemical crosslinking by photopolymerization, the PVA component was physically cross-linked through freeze/thaw cycling.

A total of nine freeze/thaw cycles were completed by freezing at −80° C. and thawing at room temperature (20° C.). After completion of freezing and thawing cycles, the hydrogels were purified by placing hydrogel samples in repeated solutions of pH 7.4 phosphate buffer saline (PBS) for 7 days wherein the PBS buffer was changed every 24 hours. A total of nine hydrogel compositions were synthesized which are outlined in Table 1.

TABLE 1

Composition of PVA double network hydrogels

| Sample Name | PVA: Anionic Hydrogel Mole Ratio | Mole Percent (%) | | | |
|---|---|---|---|---|---|
| | | AA | AMPS | AAm | MBAA |
| DNH 1 | 70:30 | 63 | 22 | 14 | 1.3 |
| DNH 2 | 85:15 | 63 | 22 | 14 | 1.3 |
| DNH 3 | 90:10 | 63 | 22 | 14 | 1.3 |
| DNH 4 | 95:5 | 63 | 22 | 14 | 1.3 |
| DNH 5 | 85:15 | 63 | 22 | 14 | 0.6 |
| DNH 6 | 85:15 | 63 | 22 | 14 | 2.5 |
| DNH 7 | 85:15 | 80 | 10 | 10 | 1.3 |
| DNH 8 | 85:15 | 10 | 80 | 10 | 1.3 |
| DNH 9 | 85:15 | 10 | 10 | 80 | 1.3 |

The double network hydrogels synthesized were varied in the PVA to anionic hydrogel mole ratio, mole percent cross-linker, and monomer composition. In addition to the formulations outlined in Table 1, a PVA hydrogel control was synthesized for cylindrical samples. These formulations consisted of a 15% and 20% PVA hydrogel formulation.

The photopolymerization depth of the hydrogels was confirmed by using the DNH 2 formulation. The hydrogel formulation was poured into a mold and polymerized under a UV lamp for 1 and 2 hours with no free-thaw cycling after the photopolymerization. Additionally, a 2 hour UV cured sample was allowed to sit out at room temperature for 20 hours prior to testing. The top and bottom 7 mm of cylindrical disks were removed to test for compressive elastic modulus. The top represents the surface closest to the UV light exposure and the bottom being the furthest.

Unconfined compression testing was conducted using an MTS Synergie 200 electromechanical material testing machine with two impermeable, unlubricated platens. Prior to mechanical testing, each sample was equilibrated in pH 7.4 PBS at 37° C. for 18 hours. Sample testing was performed at a strain rate of 100%/min in a pH 7.4 PBS at 37° C. after preloading the hydrogel samples to 0.2 N. Each sample was strained to 20% (axial). Five specimens (n=5) were tested with unconfined compression. The compressive elastic modulus was determined from the unconfined compression test by measuring the slope of the linear region in the stress-strain curve between 15% and 20% strain. All PVA double network cylindrical samples were tested immediately after freeze-thaw cycling and after drying and rehydration of the samples.

For depth dependent curing testing, all samples (n=5) were removed from the mold prior to freeze-thaw cycling. The compression testing was conducted similar to the method described herein however the samples were tested at room temperature without submersion in PBS. The compressive elastic modulus of these samples was calculated by measuring the slope of the linear region in the stress-strain curve between 15% and 20% strain.

The water content and percent swelling of the PVA double network hydrogel cylindrical samples (n=5) were determined similarly to previously reported methods (see, e.g., Maia, J. et al., Polymer (Guildf). 2005, 46 (23), 9604-9614). Following, the sample specimens were dried at 37° C. under reduced pressure until a constant weight. Residual salt in the dried samples was determined using the molarity of PBS and mass of water removed. The residual salt content was subtracted from the dry samples weight to get the final dried sample weight (md). With the above measurements, the water content and percent swelling were determined as described below.

$$WC = \frac{m_w - m_d}{m_w} \times 100\% \quad (1)$$

$$S = \frac{m_w - m_d}{m_d} \times 100\% \quad (2)$$

The crystallinity was determined using a Rigaku Ultima IV X-ray Diffractometer. The x-ray diffraction (XRD) method for determining the relative crystallinity was derived from previously outlined methods (see, e.g., Gu, W., et al., ASME-PUBLICATIONS-BED 1996, 33, 89-90; Sciarretta, V.; Nostra, C., Eur. Rev. Med. Pharmacol. Sci. 2013, 17, 3031-3038). All scans were conducted over a 2θ range of 10° to 65° at scan rate of 2.0° 2θ/s. The increased scan rate was chosen to reduce the drying and curling of the hydrogel samples during testing. A total of three samples (n=3) were tested per each material type. The sample scans were then analyzed using Rigaku PDXL XRD software. Prior to analysis, a smoothing of the results was conducted using a 15 point Savitzky-Golay filter. The method described by Ricciardi and coworkers was used to calculate the relative crystallinity with the PVA crystalline peak occurring at 2θ of 19.4° (see Ricciardi, R. et al., Macromolecules 2004, 37, 1921-1927).

Dried hydrogel cylinders were placed in PBS at 37° C. for a period of one week. Samples (n=5) were removed periodically, and the wet weight (mw) was determined by removing residual PBS from the surface with a tissue paper and weighing the samples on an analytical balance. Both water content (eq. 1) and swelling percent (eq. 2) were calculated at each time point. The swelling rate ($k_s$) and equilibrium swelling ($S_{eq}$) were determined from the second order swelling kinetics equations outlined below. All results for t/S were plotted versus time data where the slope of the line was $1/S_{eq}$ and the intercept was $1/k_S S_{eq}$.

$$\frac{dS}{dt} = k_S(S_{eq} - S)^2 \quad (3)$$

$$\frac{t}{S} = \frac{1}{k_S S_{eq}^2} + \left(\frac{1}{S_{eq}}\right)t \quad (4)$$

In addition, the free swelling diffusion coefficient for cylindrical samples (n=5) was calculated using previously described methods based on Fick's second law of diffusion (see Gures, S. et al., Eur. J. Pharm. Biopharm. 2012, 80 (1), 122-129). Using Matlab and equation (5), the experimental cylindrical water mass data (Mt/M∞) versus time was plotted in order to solve for the diffusion coefficient (D). In the equation below, Mt and M∞ are the mass of water swollen into the hydrogel at time t and infinite time. Both R and H represent the radius and height of the hydrogel cylinder, and an denote the roots for a zero order Bessel function of the first kind.

$$\frac{M_t}{M_\infty} = 1 - \frac{32}{\pi^2} * \sum_{n=1}^{\infty} \frac{1}{\alpha_n^2} * \exp\left(-\frac{\alpha_n^2}{R^2} * D * t\right) * \sum_{p=0}^{\infty} \frac{1}{(2*p+1)^2} * \exp\left(-\frac{(2*p+1)^2 * \pi^2}{H^2} * D * t\right) \quad (5)$$

The results are reported with the mean±standard deviation that included a minimum of three samples. Statistical analysis was completed using a one-way analysis of variance (ANOVA) at a 95% confidence interval. Statistical analysis was completed using Minitab statistical software with statistical significance determined at p≤0.05.

Chemical cross-linking of the anionic hydrogel component of PVA double network hydrogel formulation DNH 2 was completed using UV light exposure times of 1 and 2 hours. After photopolymerization at multiple time intervals, the top and bottom 7 mm were cut from the cylindrical samples to determine to stiffness at different depths. Table 2 outlines the compressive elastic modulus of these samples at different photopolymerization times and depths. Minimal differences between the photopolymerization times and hydrogel depths were measured through the compressive elastic modulus. While there was a significant difference (p>0.05) in test location for the samples with a photopolymerization time of 2 hours, this was likely due to the variations in sample flatness for the top of the 2 hour sample. This irregularity was caused in removing the samples from the mold, and therefore, the samples were not uniformly compressed across the whole area of the surface. In addition, the top section of samples that underwent exposure to UV light for 2 hours and 20 hour incubation were not measured as the top section of the samples could not be removed for the mold without significant deformation.

TABLE 2

Depth and time dependent polymerization of PVA DNH hydrogels (n = 5)

| Photopolymerization Time | Test Sample Location | Compressive Elastic Modulus, MPa |
|---|---|---|
| 1 hr | Top | 11.30 ± 3.94 |
|  | Bottom | 12.17 ± 5.03 |
| 2 hr | Top | 8.51 ± 0.93 |
|  | Bottom | 11.65 ± 1.37 |
| 2 hr/20 hr delay | Bottom | 12.14 ± 2.04 |

With the results described above, the PVA double network hydrogel samples were synthesized using the 2 hr. photopolymerization time. The longest UV exposure time was used in order make sure all chemically cross-link networks reacted to completion. The DNH 1 and DNH 6 PVA double network hydrogel samples were so highly cross-linked that the samples could not be removed from the mold without damaging the samples. The remaining section will therefore exclude these samples.

Figure 15:
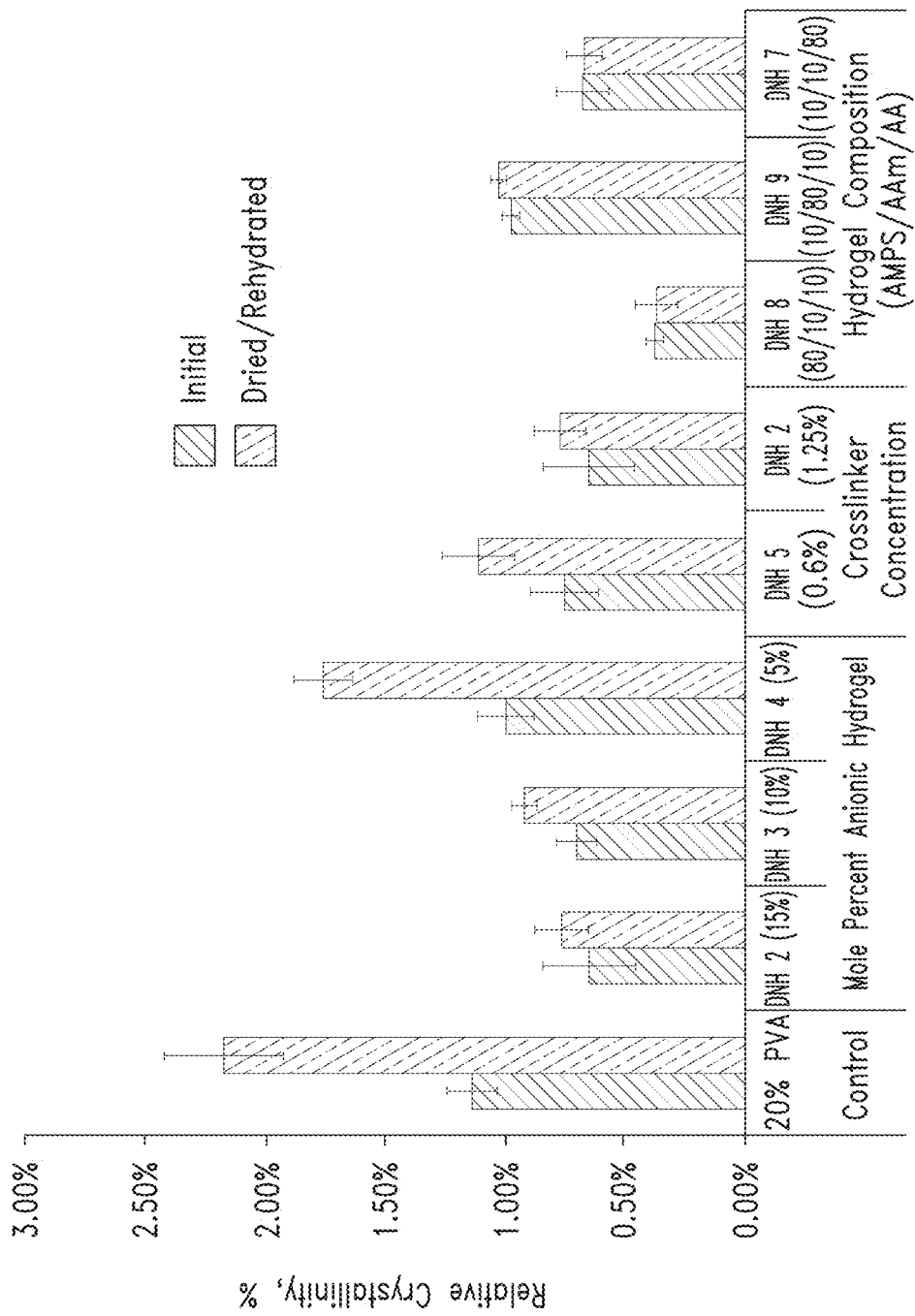
FIG. 15 shows relative crystallinity of PVA double network hydrogels of the present disclosure (mean±standard deviation, n=3).

The relative crystallinity was determined according to a previously outlined method, see Ricciardi, R. et al., Macromolecules 2004, 37, 1921-1927. A typical graph of the XRD results from a 20% PVA rehydrated sample is illustrated in FIG. 15. The overall relative crystallinity results for the PVA double network hydrogel samples and controls are shown in FIG. 15. The 20% PVA control measured in this study was comparable to results described by Holloway and colleagues for a 20% PVA hydrogel (see, Holloway, J. L. et al., Soft Matter 2013, 9, 826-833). All double network samples except DNH 4, DNH 5, and DNH 9 had a significant (p<0.05) decrease from the PVA control. In comparing samples to the control after drying and rehydration, the only sample not significantly different (p>0.05) from the PVA control was DNH 4 which had the lowest anionic hydrogel concentration. While most samples appear to show some increase in relative crystallinity after drying and rehydration, only 20% PVA, DNH 3, and DNH 4 samples showed a significant (p<0.05) increase in the relative crystallinity. Here, the DNH 4 formulation had the lowest concentration of the anionic hydrogel component, and the DNH 3 formulation had the second lowest anionic hydrogel of 10%. While not significant (p>0.05) initially, a significant (p<0.05) increase in the relative crystallinity was observed between the two cross-linker concentration after dehydration and annealing. These formulations consisted of a 15% anionic hydrogel concentration.

The composition of the anionic hydrogel component also affected the crystallinity of the PVA double network hydrogels. For comparison between hydrogel composition conditions, it is seen that the incorporation of the anionic hydrogel with a concentration of 15% causes limited changes in the relative crystallinity after drying and rehydration. The lowest relative crystallinity between DNH 7, DNH 8 and DNH 9 was in the DNH 8 formulation, which consisted primarily of the AMPS monomer. This monomer has the highest molar mass which increased the overall weight percent of the hydrogel formulation. The weight percent between DNH 9 and DNH 7 was similar, but the DNH 9 formulation had a significantly (p<0.05) greater relative crystallinity.

Figure 16:
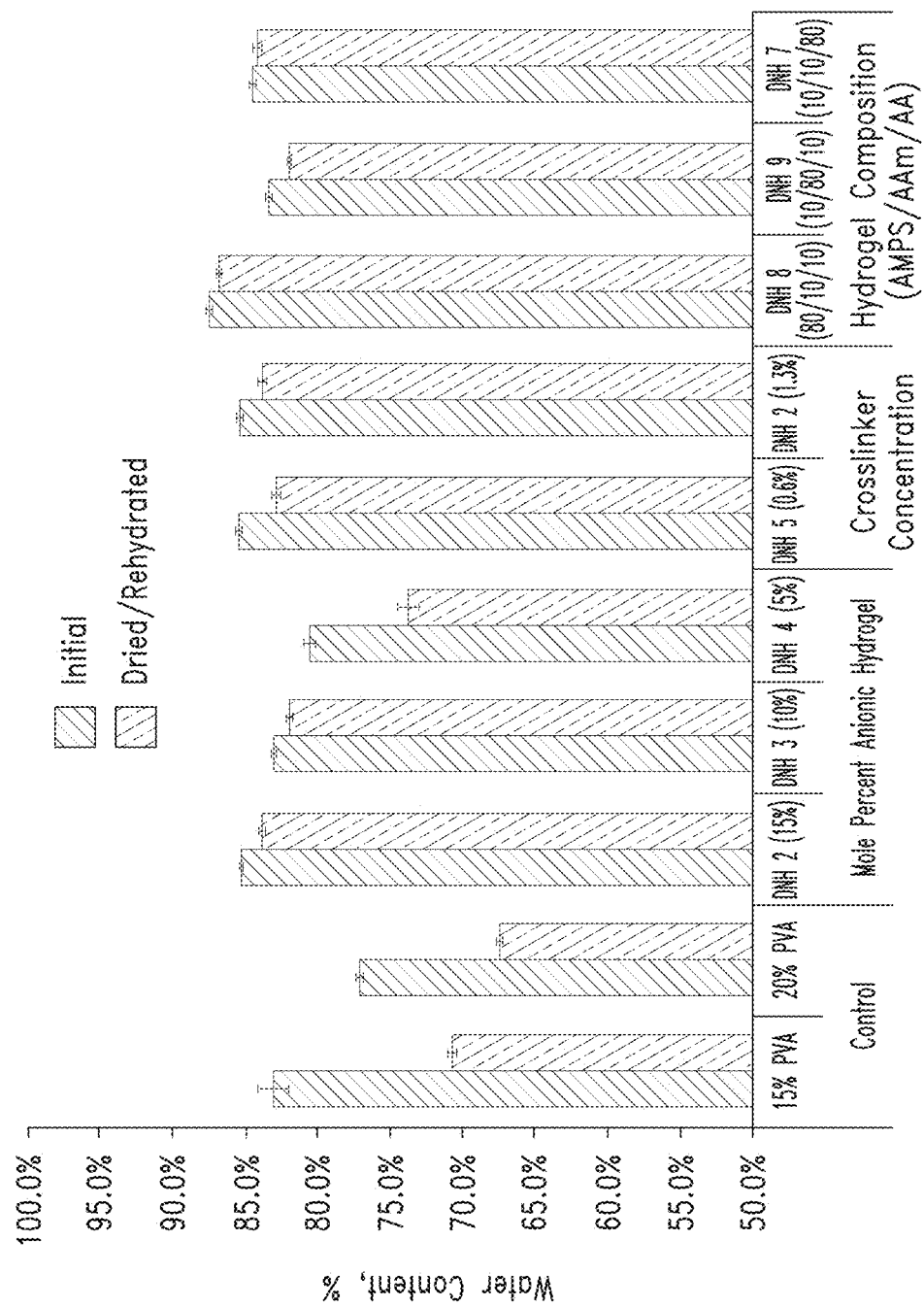
FIG. 16 shows water content of PVA double network hydrogels of the present disclosure (mean±standard deviation, n=5).

The water content of PVA double network hydrogels and controls is outlined in FIG. 16. While the PVA double network hydrogels were based on a 20% PVA solution similar to the control, each double network hydrogel formulation swelled upon placing in PBS resulting in higher water content and percent swelling. For comparison, the percent swelling was outlined below in Table 3 for all initial results. The 20% PVA hydrogel control swelled to 338.6% while the swelling of PVA double network hydrogels ranged from 414.6% to 697.1%. As the percent of anionic hydrogel increased, the water content for both the initial and dried/rehydrated samples also increased. Minimal differences were observed for the initial samples with different cross-linker concentrations. However after drying and rehydration, the sample with a lower cross-linker concentration had a lower water content which likely was a result of the increased relative crystallinity in that sample. The composition of the anionic hydrogels resulted in marked differences in the resulting water content. Both hydrogels with the highest concentrations of AMPS and AA had the highest water content with DNH 8 having an initial water content of 87.5% and DNH 7 having an initial water content of 83.4%. The hydrogel component consisting primarily acrylamide resulted in reduced water content which coincided with the highest crystallinity between DNH 7, DNH 8, and DNH 9.

TABLE 3

Percent Swelling Results of PVA double network hydrogels (n = 5)

| Sample Name | Initial Percent Swelling, % |
|---|---|
| 20% PVA | 338.6 ± 2.3 |
| DNH 2 | 581.2 ± 2.2 |
| DNH 3 | 486.2 ± 7.2 |
| DNH 4 | 414.6 ± 8.8 |
| DNH 5 | 587.4 ± 9.1 |
| DNH 7 | 543.4 ± 11 |
| DNH 8 | 697.1 ± 9.4 |
| DNH 9 | 501.2 ± 6.4 |

Figure 17:
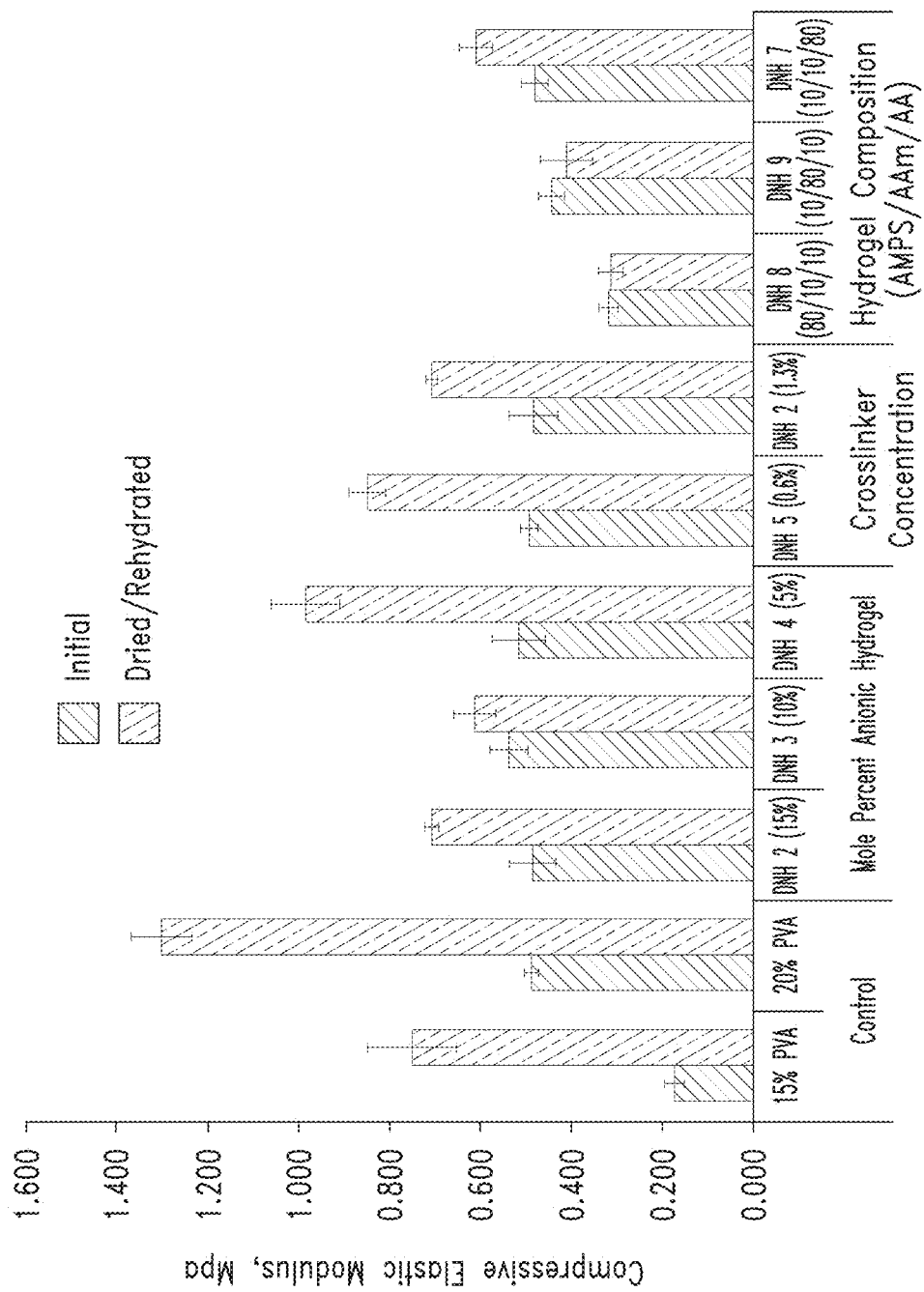
FIG. 17 shows compressive elastic modulus for PVA double network hydrogels of the present disclosure and controls (mean±standard deviation, n=5).

The PVA double network hydrogels indicated similar compressive elastic modulus to the 20% PVA hydrogel control and significant increase in modulus compared to the 15% PVA hydrogel control as displayed in FIG. 17. Both the 15% and 20% PVA hydrogel controls were included as the compressive elastic modulus has been shown to be highly dependent on the water content of PVA hydrogels, where the relationship between water content and compressive elastic modulus of PVA hydrogels has an inverse linear relationship. According to FIG. 16, all PVA double network hydrogels except DNH 4 had greater or equal water content to the 15% PVA hydrogel control, while the double network hydrogel also had a higher modulus in the initial results.

The incorporation of the anionic hydrogel under varied conditions of cross-linker concentration, hydrogel concentration, and anionic hydrogel composition had little effect on the compressive modulus when compared between all groups at initial testing. The one exception to this was the DNH 8 formulation which had a significant ($p<0.05$) decrease in compressive elastic modulus. However, after drying and rehydration, differences between each group became apparent. A significant difference ($p<0.05$) in the compressive elastic modulus was determined between the higher concentrations of anionic hydrogel of 10% and 15% and the lower concentration of 5%. Similar trends were observed between the anionic hydrogels of varied cross-linker concentrations. Here, no significant differences ($p>0.05$) were indicated at the initial testing, but after drying and rehydration, significant increases ($p<0.05$) were detected with the low amount of cross-linker seeing the larger increase in compressive elastic modulus at 72.1%.

In evaluating the effect of the composition on the compressive elastic modulus, initial testing between each group indicated no significant differences ($p>0.05$) between DNH 9 and DNH 7 but significant increases ($p<0.05$) with DNH 9 and DNH 7 over DNH 8. The formulation for DNH 8 had the highest molar concentration of AMPS, lowest crystallinity, and highest water content. Typically, the lower crystallinity and high water content would result in lower compressive modulus. Notably, even with the highest water content of all samples tested, the DNH 8 hydrogel still had a higher initial compressive modulus than a 15% PVA hydrogel. This is likely a result of the osmotic pressure effect due to the charged anionic hydrogel. After drying and rehydration, both DNH 8 and DNH 9 had no significant ($p>0.05$) differences in the compressive elastic modulus while DNH7 had a significant increase ($p<0.05$). Here, DNH 7 had both a lower relative crystallinity and higher water content than DNH 9, but resulted in an increased compressive modulus. This relationship further illustrates the effect of the anionic hydrogel component between a hydrogel consisting primarily of acrylic acid versus acrylamide. The anionic component appears to increase the compressive modulus likely through fluid pressurization from the resulting osmotic pressure.

The swelling rate and equilibrium percent swelling after drying and rehydration is outlined in Table 4 for each of the double network hydrogel compositions and the PVA control. The incorporation of the chemically cross-linked anionic hydrogel resulted in significant ($p<0.05$) increases in the equilibrium percent swelling for all of double network hydrogel formulations in comparison to the 20% PVA control. In comparing the swelling rate, DNH 2 and DNH 7 had no significant ($p>0.05$) differences from the PVA control. However, the DNH 3, DNH 4, and DNH 5 formulations significantly ($p<0.05$) increased in swelling rate, and DNH 8 decreased in the swelling rate. For samples with varied molar concentration of anionic hydrogel, the swelling rate increases, and the equilibrium percent swelling decreases with decreasing molar concentrations of the anionic hydrogel. In addition, the decreasing amount of cross-linker concentration results in a significant ($p<0.05$) increase in swelling rate and significant ($p<0.05$) decreases in equilibrium water content. The lowest swelling rate was observed in the DNH 8 formulation which subsequently had the highest equilibrium water content. The effect of composition indicated that the least amount of anionic monomer resulted in the fastest swelling rate but the lowest equilibrium water content.

TABLE 4

Free swelling rate and diffusion coefficient of PVA double network hydrogels and controls (n = 5)

| Sample Name | Equilibrium Percent Swelling, % | Swelling Rate ($10^{-4}$), $min^{-1}$ |
|---|---|---|
| 20% PVA | 233.6 ± 1.1 | 3.50 ± 0.21 |
| DNH 2 | 549.9 ± 7.0 | 3.46 ± 0.14 |
| DNH 3 | 492.2 ± 5.0 | 4.57 ± 0.49 |
| DNH 4 | 299.4 ± 9.5 | 5.79 ± 0.41 |
| DNH 5 | 510.3 ± 7.9 | 4.17 ± 0.23 |
| DNH 7 | 570.6 ± 6.9 | 3.07 ± 0.84 |
| DNH 8 | 695.5 ± 8.6 | 3.03 ± 0.27 |
| DNH 9 | 477.7 ± 3.5 | 4.49 ± 0.33 |

Figure 18:
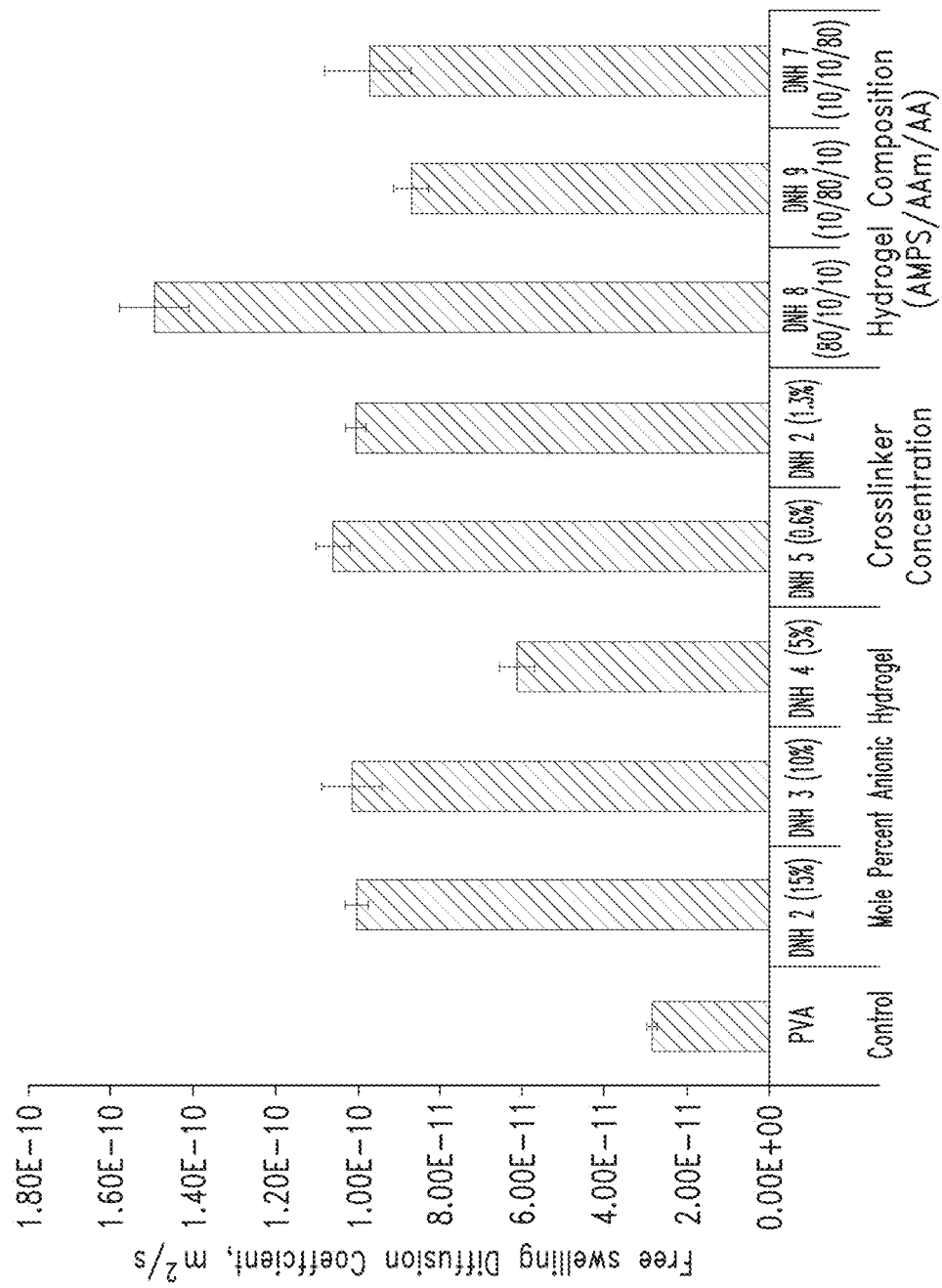
FIG. 18 shows free swelling diffusion coefficient of PVA double network hydrogels of the present disclosure and a 20% PVA hydrogel control (mean±standard deviation, n=5).

In all double network hydrogels, a significant increase ($p<0.05$) in the free swelling diffusion coefficients was observed in comparison to the 20% PVA hydrogel control as outlined in FIG. 18. While no significant differences ($p>0.05$) were indicated between DNH 2 and DNH 3, the effect of the mole percent hydrogel concentration on the diffusion coefficient was shown in DNH 4. Here, the mole percent anionic hydrogel of 5% decreased the free swelling diffusion coefficient compared to the 10% and 15%. The changes in cross-linker concentration minimally increased the diffusion coefficient between DNH 5 and DNH 2 with changes of only $1.06×10^{-10}$ versus $1.00×10^{-10}$ $m^2/s$. The highest diffusion coefficient was measured in DNH 8 which had an anionic hydrogel composition of 80/10/10 AMPS/AAm/AA. No significant differences were observed with between DNH 9 and DNH 7.

The DNH hydrogels of this Example were synthesized to demonstrate a tunable chemically cross-linked anionic hydrogel and physically cross-linked PVA hydrogel. Based on the structural component of PVA hydrogels, the structural components of the PVA double network hydrogels is expected to have a crystalline PVA region, bound water region with amorphous PVA/anionic hydrogel, and free water region in the porous structure. However as the anionic hydrogel is polymerized first, the resulting physical cross-linking of PVA structure should be affected by the chemical composition and concentrations of the anionic hydrogel. In the DN hydrogels of this Example, the molar concentration, cross-linker concentration, and composition of an anionic hydrogel in a PVA double network hydrogel was investigated to determine the effects on properties such as relative crystallinity, water content, compressive elastic modulus, swelling rate, and diffusion coefficient.

In first synthesizing the PVA double network hydrogels, the depth dependent curing of the anionic hydrogel network was confirmed. Hydrogels with exposure to UV light between 1 and 2 hours showed no differences. Subsequently, all chemically crosslinked hydrogels were polymerized for 2 hours prior to physical cross-linking by freeze-thaw cycles. During this testing, the DNH 2 formulation was used as a representative sample. Later, DNH 1 and DNH 6 formulation were polymerized under the same conditions. With the higher amounts of monomer and cross-linker, these formulations were too brittle to be removed from the mold after the freeze-thaw cycles. These formulations were therefore not pursued any further in this work.

It was observed that the relative crystallinity decreases with an increasing amount of the chemically cross-linked hydrogel network. Increases in the relative crystallinity were also observed after drying and rehydration of samples with lower cross-linker concentration. The lowest relative crystallinity was observed in DNH 8 which had a composition consisting of 80 mol % AMPS. Here, the AMPS monomer has a higher molar mass resulting in an increased weight percent hydrogel while the monomer molar concentration was constant between DNH 7, DNH 8, DNH 9 and DNH 2. Because the chemically cross-linked anionic hydrogel was polymerized prior to physically cross-linking PVA, the increased anionic hydrogel mass and cross-linker concentration inhibited PVA crystallization upon freeze-thaw cycles.

The incorporation of the anionic hydrogel network served to not only increase the water content for the PVA double network hydrogels, but also reduce the decreases in water content after drying and rehydration. Specifically, the water content of the PVA hydrogel controls were shown to decrease by 15.0% and 12.6% in the 15% PVA and 20% PVA samples, respectively, after drying and rehydration. The incorporation of the anionic hydrogels had minimal decreases in water content with the largest decrease in DNH 4 of 8.5% and the remaining samples ranging from 1.8% to 0.3%.

The compressive elastic modulus of PVA double network hydrogels appears to be a function of both the crystallinity and water content. Further, the compressive elastic modulus of PVA double network hydrogel was increased through lower anionic hydrogel and cross-linker concentrations as the relative crystallinity increased and water content reduced in these samples. The present disclosure looked at increasing the compressive elastic modulus through the tunable anionic hydrogel component which would increase the internal fluid pressurization through the Donnan osmotic pressure. This increase in the compressive elastic compressive modulus was immediately evident in the PVA double network hydrogels as they had higher water content and lower crystallinity yet comparable compressive modulus to 20% PVA hydrogels. In addition, the 15% PVA hydrogel with the closest water content to the PVA double network hydrogels had a much lower compressive elastic modulus. Comparing DNH 7 and DNH 9 samples which had an increased concentration of anionic moieties in DNH 7, the compressive modulus was greater in DNH 7 after drying and rehydration even with a lower crystallinity and higher water content than DNH 9. These results further suggest that the anionic hydrogel serves to increase the stiffness in the PVA double network hydrogels.

The free swelling diffusion coefficient of PVA hydrogels ranges between $1.90 \times 10^{-11}$ m$^2$/s and $4.11 \times 10^{-11}$ m$^2$/s and is dependent on the concentration of PVA and subsequently the relative porosity of the hydrogels. With the PVA double network hydrogels of the present disclosure, the diffusion coefficient increased in all samples compared to a PVA control through the incorporation of a second anionic hydrogel composition. One reason for the increased free swelling diffusion coefficient is the decrease in the PVA crystallinity as a result of the anionic hydrogel component. The distinct differences in the diffusion coefficient between double network hydrogel samples were most pronounced in the DNH 4 and DNH 8 formulations. These two formulations constitute an inverse relationship between the highest and lowest relative crystallinity and free swelling diffusion coefficient in the PVA double network hydrogels.

The PVA double network hydrogels of the present disclosure incorporate a negative charged component into PVA hydrogels in order to improve the stiffness similar to the contribution of GAG in articular cartilage. The results in this Example indicate that this can be accomplished through the incorporation of the tunable anionic copolymer hydrogel into a PVA double network hydrogels.

In this Example, novel double network hydrogel formulations were synthesized by first creating a semi-IPN by the photopolymerization of a tunable anionic hydrogel. Afterwards, trapped PVA in the anionic hydrogel was physically cross-linked through freeze thaw cycles which imparted crystallization of the PVA. The chemically cross-linked anionic hydrogel inhibited crystallinity of the PVA. Specifically, the anionic hydrogel compositions with increasing anionic hydrogel concentration, cross-linker concentration, and molar mass of monomer reduced the crystallinity of PVA especially after dehydration and rehydration of the double network hydrogels. With the reduction in crystallinity, the incorporation of the anionic hydrogel resulted in an increase in water content with values ranging from 73.8% to 87.5%. The incorporation of the anionic hydrogel for purposes of mimicking GAG functionality served to increase the stiffness of the PVA double network hydrogel formulations. This effect was illustrated through the increases in the compressive elastic modulus in comparison to PVA hydrogel controls of comparable water content. The double network hydrogel formulations had a compressive elastic modulus ranging from 0.317 MPa to 0.986 MPa which was dependent on the formulation and hydration conditions. For comparison, the typical Young's modulus for articular cartilage ranges from 0.45-0.80 MPa25. In addition to compressive modulus, all PVA double network hydrogel formulations had increased free swelling diffusion coefficient and overall water content. These results demonstrate that PVA double network hydrogels can be synthesized to both increase water content and improve the compressive elastic modulus by the incorporation of a tunable anionic hydrogel into PVA hydrogels.

The measurement of the relative coefficient of friction ($\mu$, RCOF) was adopted from a previous method reported by Gong and coworkers (Gong, J. P. et al., J. Phys. Chem. B 1999, 103, 6007-6014). Before attachment of the sample to the fixture, all samples were equilibrated at 37° C. for 18 hours in PBS. For attachment, the hydrogel samples were blotted dry on one side and glued to a parallel plate fixture with cyanoacrylate glue. In addition, a glass plate was attached to the bottom fixture. In this work, the torque (c), normal force (N), angular velocity (w) and temperature (T) were measured by an Anton Paar MCR 301 rheometer. The set conditions for this testing involved a temperature of 37° C., normal force of 3 N, and angular velocity of 0.1 rad/s. The output value from the rheometer was the torque. Prior to testing, the diameter and subsequently radius (R) of each hydrogel sample was measured using calipers. Afterwards, a total of three samples (n=3) per group were tested for 120 minutes. With the measured values of torque and normal force, the frictional force (F) was calculated based on the equations described by Gong and colleagues, and the relative coefficient of friction could then be determined with the frictional force as outlined by the equations below. The relative coefficient of friction results were reported as initial values, average over the first 90 sec, and average over the last 30 minutes. In addition, a running average of the relative coefficient of friction values was determined and plotted with the mean and standard deviation.

$$F = \frac{4*\tau}{3*R} \quad (1)$$

$$\mu = \frac{F}{N} \quad (2)$$

In order to analyze the hydrogel structure, the cross-section of the hydrogels was imaged using a Hitachi S4800 scanning electron microscope (SEM). The hydrogels were prepared by placing the samples in liquid nitrogen after equilibration in PBS. The samples were cryo-fractured and thawed at room temperature. After thawing, the hydrogels were dehydrated by placing the samples for 60 minutes per solution in subsequent aqueous solutions of 70%, 85%, 95%, and 100% ethanol. Afterwards, the PVA hydrogels were submersed in hexamethyldisilazane for 60 minutes. The samples were removed and allowed to dry at room temperature for 20 hours. Dehydrated samples were platinum sputter coated and imaged on a dry stage. The relative porosity by pore area was determined using Image J software with a total of three (n=3) image locations.

The DNH 3, DNH 4, and 20% PVA hydrogel samples were evaluated for in vitro cytotoxicity according to modified version of the International Standardization Organization (ISO) 10993-5 (Tests for In Vitro Cytotoxicity) outlining tests for in vitro cytotoxicity (see International Organizational for Standardization, (2009) International Standard ISO 10993-5 Biological evaluation of medical devices—Part 5: Tests for cytotoxicity: in vitro methods; Geneve, Switzerland: International Organization for Standardization). In this work, a negative control of UHMWPE and media only was utilized, and the positive control was a natural latex rubber. All samples and controls (n=5) were incubated at an extraction ratio of 0.2 mg/ml (sample: media) in Eagle's minimum essential medium (EMEM) containing 10% horse serum (HS) and 1% penicillin-streptomycin (pen-strep) for 24 hours at 37° C.

The cell line used for these studies was a L929 mouse fibroblast. Prior to adding the extracted eluent, cells were seeded at an initial density of $1.25\times10^5$ cells/ml in 96 well plates with 100 µl per well of the EMEM containing 10% HS and 1% pen-strep. The cells were incubated for 24 hours at 37° C. with 5% $CO_2$. Afterwards, the media was discarded, and the extracted eluents were added to the 96 well plates with five well plates per each sample/control. The cells were then incubated for an additional 24 hours at 37° C. with 5% $CO_2$. At the 24 hour time point, the cells were imaged using a Motic AE31 light microscope at 100× magnification. The grading criteria are described in Table 5. After imaging, 0.01 ml of 3-(4,5-dimethylthiazol-2-yl)-2,5-diphenyl tetrazolium bromide (MTT) solution was added to each well and incubated for 2 hours. After 2 hours, 100 µl of isopropanol with 0.04 N hydrochloric acid (HCl) was added to each well and mixed thoroughly. The absorbance value was then measured at 570 nm using a BIO-RAD Model 550 microplate reader. The cell cytotoxicity from the MTT assay was determined by subtracting the absorbance of the media blank wells without cells present from the absorbance readings of the sample wells with cells present.

TABLE 5

Grading of cytotoxicity of extracts by imaging

| Grade | Reactivity | Conditions of all cultures |
|---|---|---|
| 0 | None | Discrete intracytoplasmatic granules, no cell lysis, no reduction of cell growth |
| 1 | Slight | Not more than 20% of the cells are round, loosely attached and without intracytoplasmatic granules, or show changes in morphology; occasional lysed cells are present; only slight growth inhibition observable. |
| 2 | Mild | Not more than 50% of the cells are round, devoid of intracytoplasmatic granules, no extensive cell lysis; not more than 50% growth inhibition observable. |
| 3 | Moderate | Not more then 70% of the cell layers contain rounded cells or are lysed; cell layers not completely destroyed, but more than 50% growth inhibition observable. |
| 4 | Severe | Nearly complete or complete destruction of the cell layers. |

In order to assess the foreign body response to PVA double network hydrogels, samples were implanted in the subcutaneous tissue of Sprague-Dawley rats weighing between 200 g and 250 g. The implanted articles consisted of two PVA double network hydrogel formulations (DNH 3, DNH 4) and two controls of 20% PVA and UHMWPE. A 20% PVA hydrogel control (hydrophilic) was selected due to the similarity of the double network system but without the chemically cross-linked component. Samples of each material were cut into cylinders with a diameter of 10 mm and thickness of 1-2 mm. The rats were anesthetized, and four small incisions were made along the back to implant one of each implant in either the thoracic or lumbar regions. Five animals were sacrificed at each time point of 3 days and 28 days. The implanted articles with surrounding tissue was harvested and stored in a 10% formalin solution. After embedding in paraffin, each specimen was sectioned to 7 µm and subsequently stained with hematoxylin and eosin (H&E). The histology slides of each implant were evaluated by a licensed pathologist, and a histological score was assigned to the observed inflammatory response. Each sample was graded with a severity grade (0=no observation, 0.5=very minimal, 1=minimal, 2=mild, 3=moderate, and 4=severe). All samples were graded for (1) fibrosis, capsule (collagen formation around each implant), (2) neovascularity (formation/in-growth of new blood vessels into the implant site), (3) hemorrhage, (4) macrophage infiltrates, (5) lymphocyte infiltrates, (6) neutrophil infiltrates (7) eosinophil infiltrates (8) multinucleated giant cells, and (9) necrotic debris. In addition to severity grade, each sample was assigned a composite score which was the sum of all the categories for a given sample. Sample grading without a reported number was a result of no observations (severity grade of 0) from the specimen. The sample size at each time point was n=5 unless otherwise stated.

Statistical evaluation of results for the relative porosity, relative coefficient of friction, and MTT assay was conducted using one-way analysis of variance (ANOVA). Analysis between sample groups for the in vitro cytotoxicity scoring and in vivo histological scoring was determined using a Wilcoxon signed-rank test. Minitab statistical software was used for all statistical analysis, and statistical significance was determined at a $p \leq 0.05$.

Figure 19:
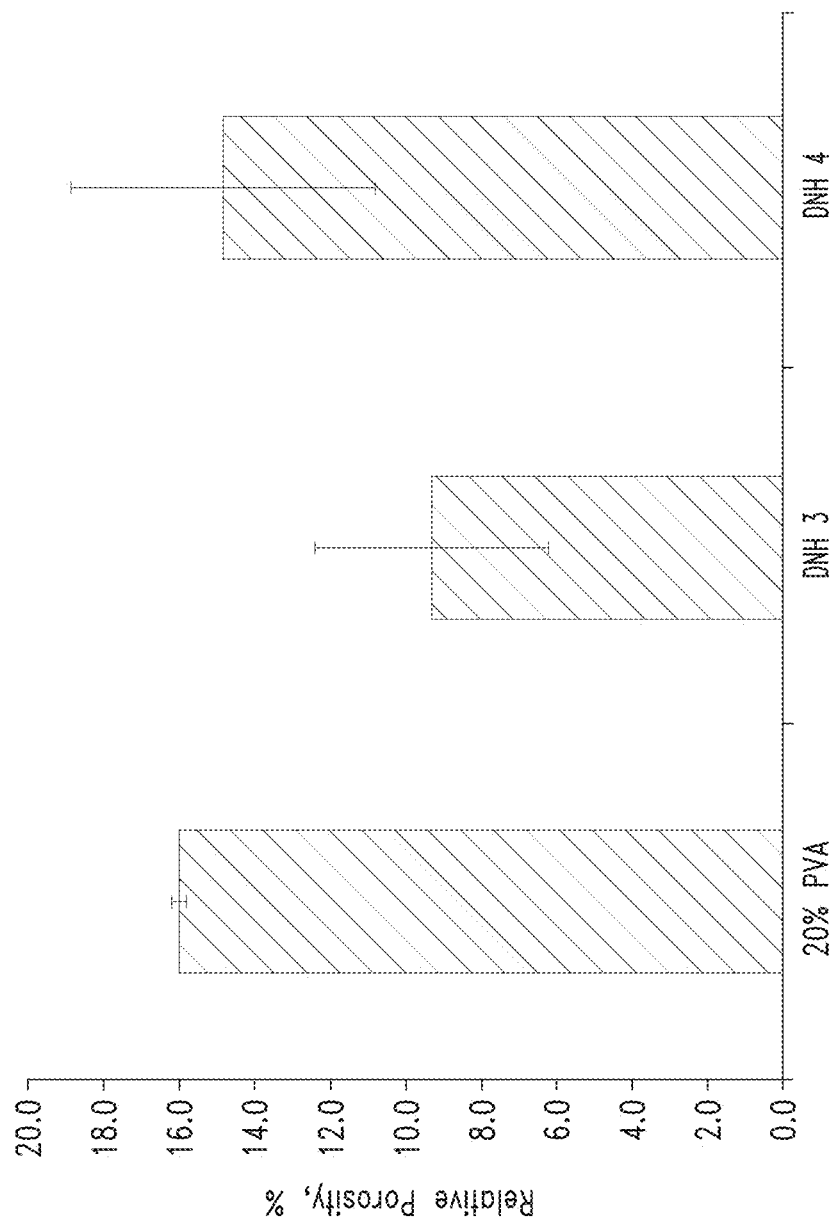
FIG. 19 shows relative porosity of PVA double network hydrogels and a PVA hydrogel control (mean±standard deviation, n=3).

The relative porosity of each hydrogel sample was determined through evaluating the percent area of pores through SEM images at a 4500× magnification. As reported in FIG. 19, the 20% PVA hydrogel control had the highest relative porosity but was not significantly ($p > 0.05$) greater than either of the DNH formulations. The relative porosity for the DNH formulations exhibited a higher standard deviation than the PVA control. For the DN formulations, the porous structure exhibited domains of highly porous regions and regions where little to no pores were present. SEM images at a magnification of 300× illustrated a scattered porous structure. In these images, the PVA hydrogel control exhibited the most homogenous porous structure, and the DNHH 3 formulation appears to have the largest amount of non-porous regions.

As described in Table 6, the relative coefficient of friction for 20% PVA, DNH 3, and DNH 4 was reported at three different time intervals to evaluate the change with time. The initial results for the relative coefficient of friction indicate no significant ($p > 0.05$) differences between the groups. Comparison of the relative coefficient of friction results over the first 90 seconds yielded the same result of no significant ($p > 0.05$) differences. However in the final 30 minutes, differences between each formulation became apparent with both DNH formulations significantly ($p < 0.05$) lower than the 20% PVA hydrogel control. In addition, the DNH 3 formulation with the highest concentration of the anionic hydrogel component had a significantly ($P < 0.05$) lower relative coefficient of friction than the DNH 4 formulation in the final 30 minutes.

TABLE 6

Relative coefficient of friction for PVA double network hydrogel and a PVA hydrogel control (n = 3).

| Sample Name | Relative Coefficient of Friction | | |
|---|---|---|---|
| | Initial | 90 sec | Final 30 min. |
| 20% PVA (control) | 0.052 ± 0.015 | 0.065 ± 0.017 | 0.151 ± 0.019 |
| DNH 3 | 0.058 ± 0.013 | 0.077 ± 0.013 | 0.080 ± 0.007 |
| DNH 4 | 0.036 ± 0.019 | 0.043 ± 0.018 | 0.099 ± 0.009 |

Figure 20A:
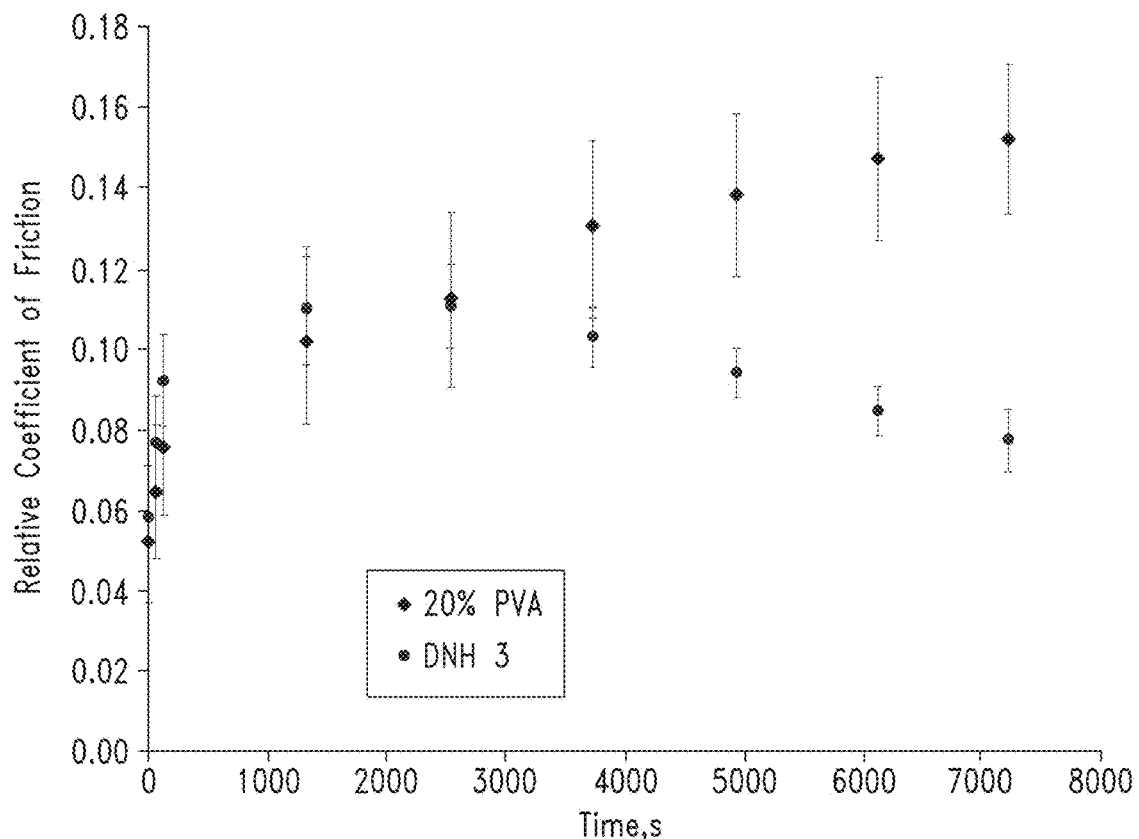
FIG. 20A-B show a comparison of the relative coefficient of friction for FIG. 20A: DNH 3.
Figure 20B:
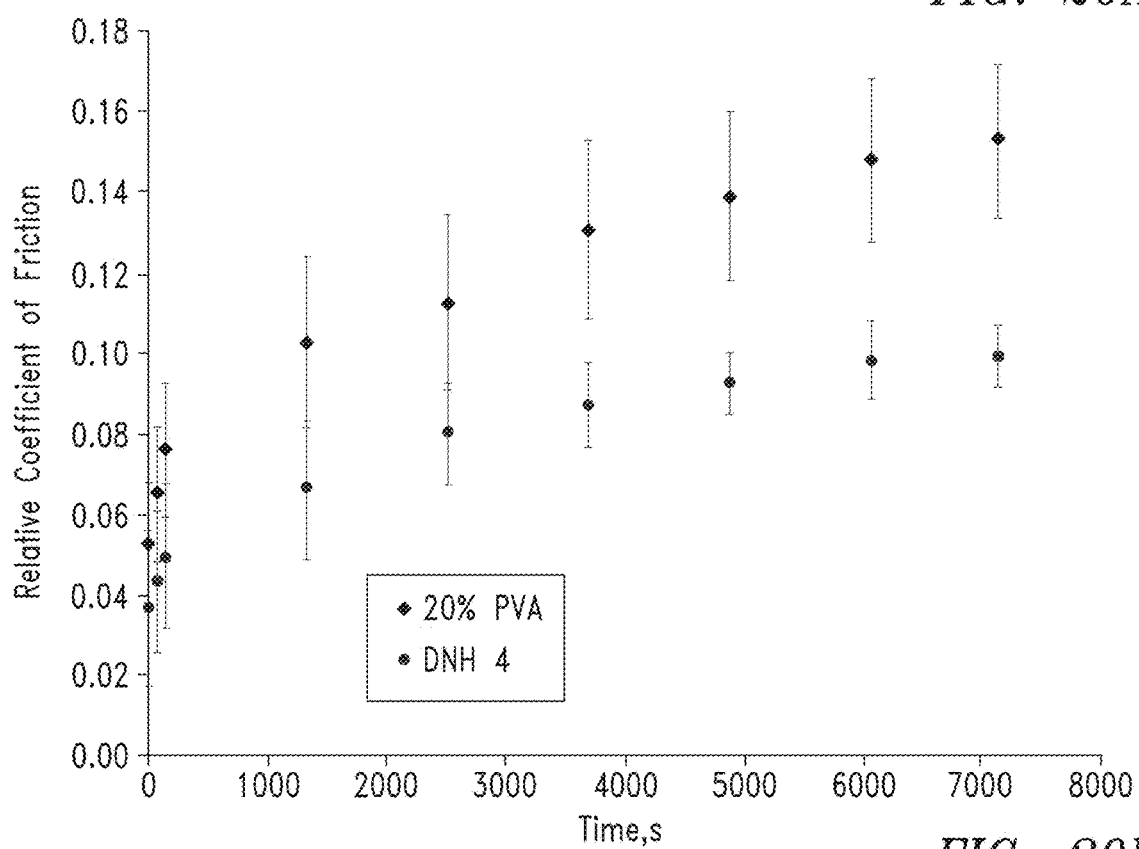

The plot of the moving average for relative coefficient of friction of all of the formulations is displayed in FIG. 20. In this Figure, each DNH formulation was compared to the 20% PVA hydrogel control. Two separate trends were noted between DNH 3 and DNH 4. In the DNH 3 formulation, the relative coefficient of friction quickly increases above 0.1 similar to the PVA hydrogel control. However between the 1000-2000 second interval, the DNH 3 formulation begins to continuously decrease for the remainder of the testing period. The DNH 4 formulation seems to follow the trend of the PVA hydrogel control which continuously increased over the full test. However, the DNH 4 formulation increased at a slower rate never increasing above a RCOF of 0.1.

Figures 21A, 21B:
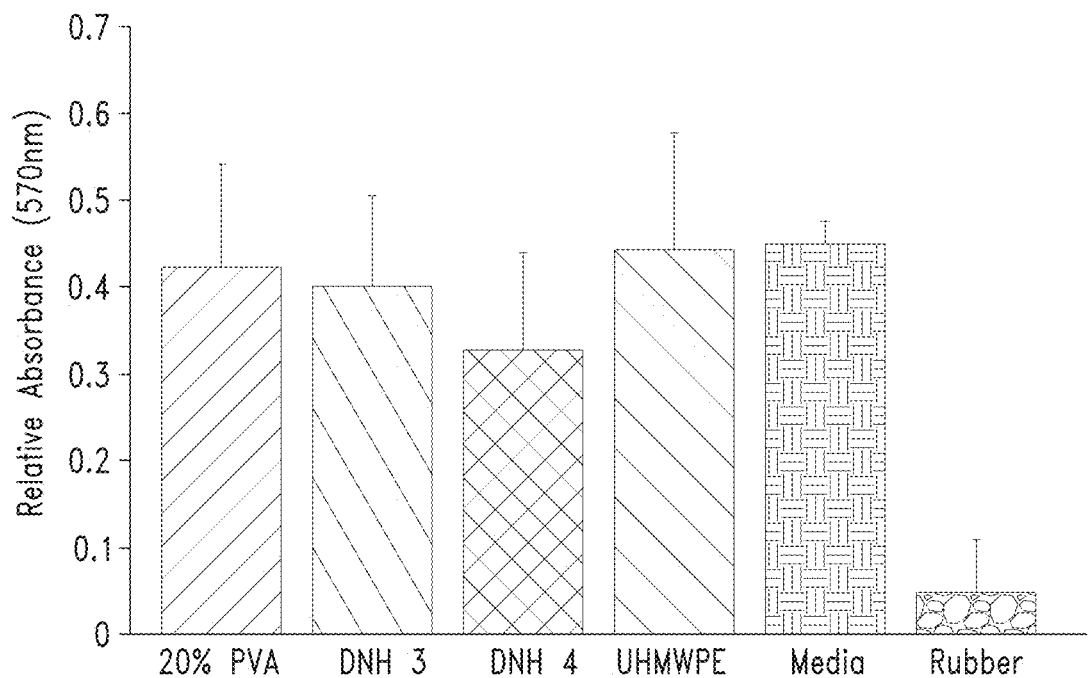
FIG. 21A-B show in-vitro result by FIG. 21A: absorbance from MTT assay

The results for both the MTT assay and qualitative scoring for in vitro cytotoxicity are displayed in FIG. 21. The MTT assay indicated no significant differences ($p > 0.05$) between the DNH 3 and DNH 4 formulations in comparison to all of the negative control groups including 20% PVA, UHMWPE, and media. In this assay, the positive control group of natural latex rubber was the only mean significantly different ($p < 0.05$) from all other groups. For comparison of scoring, the DNH3 formulation displayed no response of reactivity, and the DNH 4 formulation elicited a slight response. In this scoring, any score greater that 2 are typically considered a cytotoxic response. All DNH formulations and negative controls had a median score below 2, and the positive control had a median score of 4 (severe).

Four different materials of UHMWPE, PVA, DNH 3, and DNH 4 were implanted into the subcutaneous tissue layer of Sprague-Dawley rats. At 3 days (acute response), gross observations at explantation indicated that the implant was encapsulated in a thin tissue capsule indicating all of the materials were well tolerated. As outlined by the median severity score in Table 7, all samples had a mild to minimal response from macrophages, and the 20% PVA and UMWPE samples indicated minimal response from eosinophils. No observations of eosinophils were noted in both DNH formulations. Eosinophil infiltrate in the 20% PVA samples was observed. One additional observation was made for the DNH 4 formulation in that foamy macrophages were present that were likely attributed to some leachable component from DNH 4. Similar to the in vitro study, no significant ($p > 0.05$) differences were observed between the DNH formulations and the controls of 20% PVA and UHMWPE.

TABLE 7

Median severity for the in vivo tissue response of DNH formulations and controls (n = 5).

| Sample Name | Time Period, days | Median Severity Score | | | | Overall Composite Score |
|---|---|---|---|---|---|---|
| | | Fibrosis | Macrophages | Lymphocytes | Eosinophils | |
| UHMWPE | 3* | 0 | 1.5 | 0 | 0.5 | 2.0 |
| | 28* | 1 | 0.5 | 0 | 0 | 1.5 |
| 20% PVA | 3 | 0 | 2 | 0 | 1 | 3.0 |
| | 28** | 1 | 1 | 0 | 0 | 2.0 |
| DNH 3 | 3* | 0 | 1 | 0 | 0 | 1.0 |
| | 28* | 1 | 0.5 | 0 | 0 | 1.5 |
| DNH 4 | 3 | 0 | 1 | 0 | 0 | 1.0 |
| | 28 | 1 | 1 | 0 | 0 | 2.0 |

*n = 4,
**n = 3

The 20% PVA, DNH 3, and DNH 4 samples had a thin tissue capsule while the UHMWPE was slightly thicker. One key difference in the 28 day histological findings was the appearance of fibrosis which was absent at 3 days. In addition, the overall cell infiltrate for all samples decreased. The foamy macrophages apparent in the 3 day samples for the DNH 4 formulation were no longer visible at 28 days. In comparison of groups, no significant ($p > 0.05$) differences were detected between the DNH formulations and controls. Additionally, all sample tested in this study were well tolerated at 28 days with minimal to mild tissue response in the subcutaneous layer.

In the present disclosure, PVA double network hydrogels were synthesized using a chemically cross-linked tunable anionic copolymer and a physically cross-linked PVA hydrogel. In this work, the anionic hydrogel component was varied in overall concentration, cross-linker concentration, and composition. These new PVA double network hydrogel compositions exhibited a higher compressive elastic modulus than comparable PVA hydrogels with similar water content. Therefore, the DN formulations presented new ways to increase the compressive elastic modulus without large reductions in the water content. With these DNH formulations, this work investigated the porous structure, coefficient of friction, in vitro cytotoxicity, and in vivo tissue response. We observed that the chemically cross-linked anionic hydrogel stabilized the porous structure, the combination of stabilized porous structure and high water content resulted in a low coefficient of friction, and the DN hydrogels had a low tissue response and low cytotoxicity due to being hydrophilic and anionic.

In the present Example, the PVA double network hydrogels were not annealed but swelled directly after completion of physical crosslinking through freeze-thaw cycles. The results for the relative porosity of PVA hydrogels indicated higher standard deviations in the DNH formulations, and SEM images at 300× magnification further qualitatively illustrated the variability in the porous regions throughout the DNH hydrogels, i.e., an uneven porous structure was observed. As mentioned previously, these DNH hydrogel formulations did not undergo an annealing process which reduced the dimensional stability with lower crystallinity in the PVA. DNH hydrogels with a higher concentration of anionic monomer result in greater swelling which could have aided in pore collapse.

The relative coefficient of friction for the DNH formulations was comparable to the 20% PVA hydrogel control at short time intervals. However, the DNH 3 and DNH 4 formulations had a reduced relative coefficient of friction for the final 30 minutes of the 2 hour testing. The relative coefficient of friction at long time intervals (>90 min.) for the DNH formulations leveled off at values significantly lower than the 20% PVA hydrogels. It is interesting to note that the DNH 3 formulation with reduced relative porosity rapidly increased in coefficient of friction initially but decreased continuously after reaching a maximum.

While not intending to be bound by this explanation, it is suggested that the differences in the relative coefficient of friction between the DNH formulations and a PVA control could be a result of two different mechanisms. A reduction in coefficient of friction for cartilage may be a result of the increased internal fluid pressurization where the osmotic pressure was modulated through different concentrations of salt solutions. Other potential reasons for the decreased coefficient of friction are the effect of the attractive or repulsive forces between two opposing surface. Here, it would be expected that an increase in the anionic hydrogel component in PVA double network hydrogel would decrease the coefficient of friction as the opposing surface of glass should have a negative charge. Noteworthy is that the DNH 3 formulation which had the highest concentration of the anionic hydrogel resulted in the lowest relative coefficient of friction at the longer time intervals.

The in vitro cytotoxicity testing indicated no significant differences between the DNH formulations and the negative controls for the absorbance through the MTT assay. By cytotoxicity grading, both of the DNH formulation's response was slight (1) to none (0). While not significant, the DNH 4 formulation had both a slightly higher cytotoxicity grade and slightly lower absorbance under the MTT assay. This is believed to be a product of some release of reactive by-products (i.e., cross-linker, monomer, and photo-initiator) from the DNH 4 formulation. The difference here, in comparison to the DNH 3 formulation, was that DNH 4 exhibited increased relative crystallinity and decreased free swelling diffusion coefficient, likely resulting in slower diffusion of residual reactive byproducts from the DNH 4 hydrogel samples. Advantageously, DNH 4 formulations may benefit from additional time for purification.

The histological findings from the in vivo subcutaneous implantations indicate that the DNH formulations and controls were well tolerated at both the acute (3 day) and subacute (28 day) time points. All samples exhibited a mild to minimal response at both time points. The slightly different tissue responses in the 20% PVA and UMWPE is hypothesized to be a result of the higher stiffness in those samples which may have caused irritation. Additionally, the foamy macrophages observed in the 3 day time point for the DNH 4 suggest the release of residual monomer or photoinitiator. This result coincides with the findings from the in vitro cytotoxicity testing for DNH 4. However by 28 days, no additional observation of foamy macrophages were present indicating the issue was resolved between the 3 day and 28 day time point.

From the results of this Example, no significant differences ($p > 0.05$) between the DNH formulations and the controls were detected in the 3-day and 28-day time points. While in some instances the 20% PVA and UHMWPE had higher scores, the sample size was not high enough to detect these differences. In addition, issues arose during sectioning which resulted in samples specimens that could not be used for scoring. This problem was likely a result of the sample thickness and mismatch in modulus between the paraffin embedding agent and sample material. Samples were prepared with a thickness of 2 mm so that they could be easily located at explantation, and no confusion would occur between the four samples per rat. However, the thickness of these samples presented a major challenge in sectioning due to the toughness of the material. The hard, thick implants curled upon sectioning, which made it difficult to obtain sectioned samples that included the implant material. Thin films less than 1 mm in thickness and different embedding material with a greater stiffness than paraffin may be utilized.

All references disclosed herein, including patent references and non-patent references, are hereby incorporated by reference in their entirety as if each was incorporated individually.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents, i.e., one or more, unless the content and context clearly dictates otherwise. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

Any headings used within this document are only being utilized to expedite its review by the reader, and should not be construed as limiting the invention or claims in any manner. Thus, the headings and Abstract of the Disclosure provided herein are for convenience only and do not interpret the scope or meaning of the embodiments.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the presently described invention. The publications discussed the text are provided solely for their disclosure prior to the filing date of the present application. Nothing herein is to be construed as an admission that the inventors are not entitled to antedate any referenced publication by virtue of prior invention.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Furthermore, the written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicant.

What is claimed is:

1. A double network hydrogel comprising a first network and a second network, the first network comprising a first polymer comprising —$CH_2$—$CH(OH)$— units; the second network comprising a second polymer comprising carboxyl (COOH)-containing units or salts thereof, sulfonyl ($SO_3H$)- containing units or salts thereof, and hydroxyl (OH)-containing units derived from N-(tris(hydroxymethyl)methyl) acrylamide, wherein the first polymer is non-identical to the second polymer, and where the first network is in combination with the second network so as to form the double network hydrogel.

2. The hydrogel of claim 1 wherein the first polymer is a polyvinylalcohol or a copolymer including —CH2-CH(OH)-units.

3. The hydrogel of claim 1 wherein the carboxyl-containing units are derived from a monomer selected from acrylic acid (AA) and methacrylic acid (MA).

4. The hydrogel of claim 1 wherein the sulfonyl-containing units are derived from a monomer selected from 3-sulfopropyl methacrylate, 3-sulfopropyl acrylate, 2-sulfoethyl methacrylate, 2-propene-1-sulfonic acid, and 2-acrylamido-2-methylpropane sulfonic acid (AMPS).

5. The hydrogel of claim 1 wherein the second polymer comprises amino-containing units derived from acrylamide (AAm).

6. The hydrogel of claim 1 wherein the first polymer is polyvinylalcohol and the second polymer is formed from monomers including each of AA, AMPS and AAm.

7. The hydrogel of claim 1 wherein the first polymer is made from x moles of monomer(s) and the second polymer is made from y moles of monomer(s), and $x/(x+y)$ is at least 0.7.

8. The hydrogel of claim 1 wherein the first network is physically crosslinked by multiple freeze thaw cycles.

9. The hydrogel of claim 1 wherein the second network is chemically crosslinked.

10. The hydrogel of claim 1 wherein the second network is chemically crosslinked with N,N'-methylenebisacrylamide (MBAA).

11. The hydrogel of claim 1 wherein the second polymer comprises crosslinking units derived from a crosslinking agent, and the crosslinking agent provides not more than 2.5 molar units when the carboxyl (COOH)-containing units or salts thereof, the sulfonyl (SO3H)-containing units or salts thereof, the hydroxyl (OH)-containing units derived from N-(tris (hydroxymethyl) methyl) acrylamide, and the crosslinking units provide a total of 100 molar units.

12. The hydrogel of claim 1 in the form of a hybrid double network hydrogel wherein the first network is physically crosslinked and the second network is chemically crosslinked.

13. A composition comprising the hydrogel of claim 1 and water.

14. The composition of claim 13 in sterile form.

15. The composition of claim 13 which exhibits a poroelastic response.

16. A method of improving an animal joint where the joint comprises cartilage, the method comprising placing a hydrogel according to claim 1 in the joint to provide a synthetic cartilage for the joint.

* * * * *